(12) United States Patent
Yoon

(10) Patent No.: US 6,387,043 B1
(45) Date of Patent: May 14, 2002

(54) PENETRATING ENDOSCOPE AND ENDOSCOPIC SURGICAL INSTRUMENT WITH CMOS IMAGE SENSOR AND DISPLAY

(76) Inventor: InBae Yoon, 11886 Farside Rd., Ellicott City, MD (US) 21042

( * ) Notice: Subject to any disclaimer, the term of this patent is extended or adjusted under 35 U.S.C. 154(b) by 0 days.

(21) Appl. No.: 09/310,112

(22) Filed: May 12, 1999

Related U.S. Application Data

(60) Provisional application No. 60/085,243, filed on May 13, 1998, provisional application No. 60/085,242, filed on May 13, 1998, and provisional application No. 60/093,069, filed on Jul. 16, 1998.

(51) Int. Cl.$^7$ .................................................. A61B 1/05
(52) U.S. Cl. ........................ 600/109; 600/129; 600/114; 600/104
(58) Field of Search ................................. 600/121, 109, 600/176, 129, 114, 104, 106, 160; 606/205

(56) References Cited

U.S. PATENT DOCUMENTS

| | | | | |
|---|---|---|---|---|
| 5,373,317 A | * | 12/1994 | Salvati et al. .................. 348/65 |
| 5,467,762 A | * | 11/1995 | Sauer et al. ................. 600/114 |
| 5,591,192 A | * | 1/1997 | Privitera et al. ............ 600/114 |
| 5,609,562 A | * | 3/1997 | Kaali .......................... 600/114 |
| 5,684,820 A | * | 11/1997 | Riek et al. ................... 600/114 |
| 5,734,418 A | * | 3/1998 | Danna .......................... 348/76 |
| 5,810,876 A | * | 9/1998 | Kelleher ...................... 606/205 |
| 5,817,061 A | * | 10/1998 | Goodwin et al. ............ 600/121 |
| 5,873,814 A | * | 2/1999 | Adair .......................... 600/109 |
| 5,891,013 A | * | 4/1999 | Thompson ................... 600/109 |
| 5,928,137 A | * | 7/1999 | Green .......................... 600/106 |
| 5,929,901 A | * | 7/1999 | Adair et al. ................. 600/109 |
| 6,086,528 A | * | 7/2000 | Adair .......................... 600/110 |
| 6,221,007 B1 | * | 4/2001 | Green .......................... 600/106 |

* cited by examiner

*Primary Examiner*—John P. Leubecker
(74) *Attorney, Agent, or Firm*—Blank Rome Comisky & McCauley LLP

(57) ABSTRACT

A penetrating endoscope provides visualization of organ or tissue structures or foreign objects in a body. The penetrating endoscope includes an elongate penetrating member, a complementary metal dioxide semiconductor (CMOS) image sensor and an objective lens. The CMOS image sensor is substantially planar and includes a plurality of pixels with a pixel signal processing circuit for generating a color image ready signal. The CMOS image sensor converts image light energy into electrical color image ready signal energy for transmission out of the body. The color image ready signal is viewed on a color image display. The CMOS image sensor is carried on the elongate penetrating member adjacent a distal end of the elongate penetrating member. The objective lens is also carried on the distal end of the elongate penetrating member on an optical axis and focuses an image corresponding to an endoscope field of view at an image plane intersecting the optical axis. The CMOS image sensor is mounted with the CMOS image sensor pixels disposed substantially in the image plane and on the optical axis. The penetrating endoscope may include end effectors such as cutters and forceps.

88 Claims, 22 Drawing Sheets

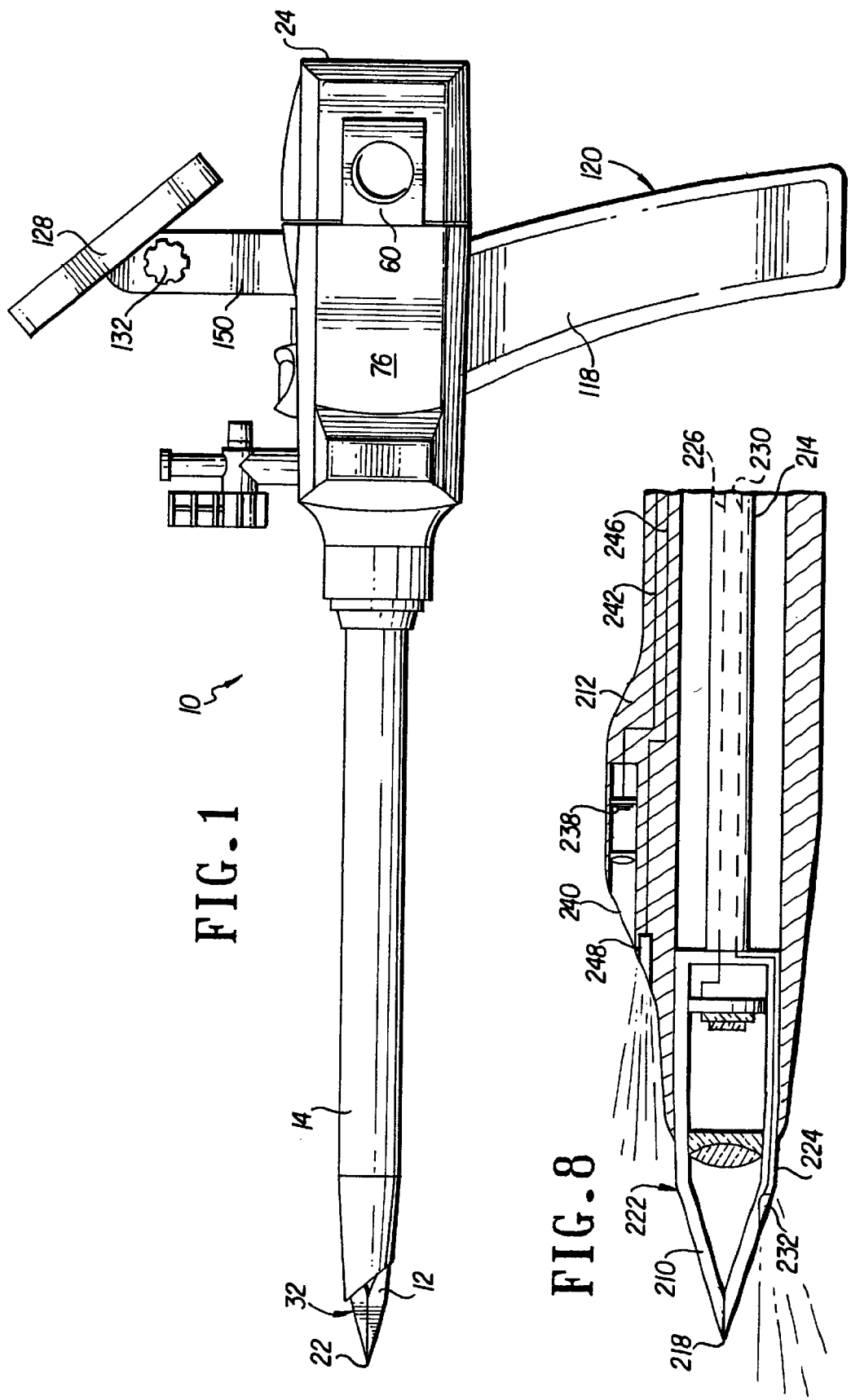

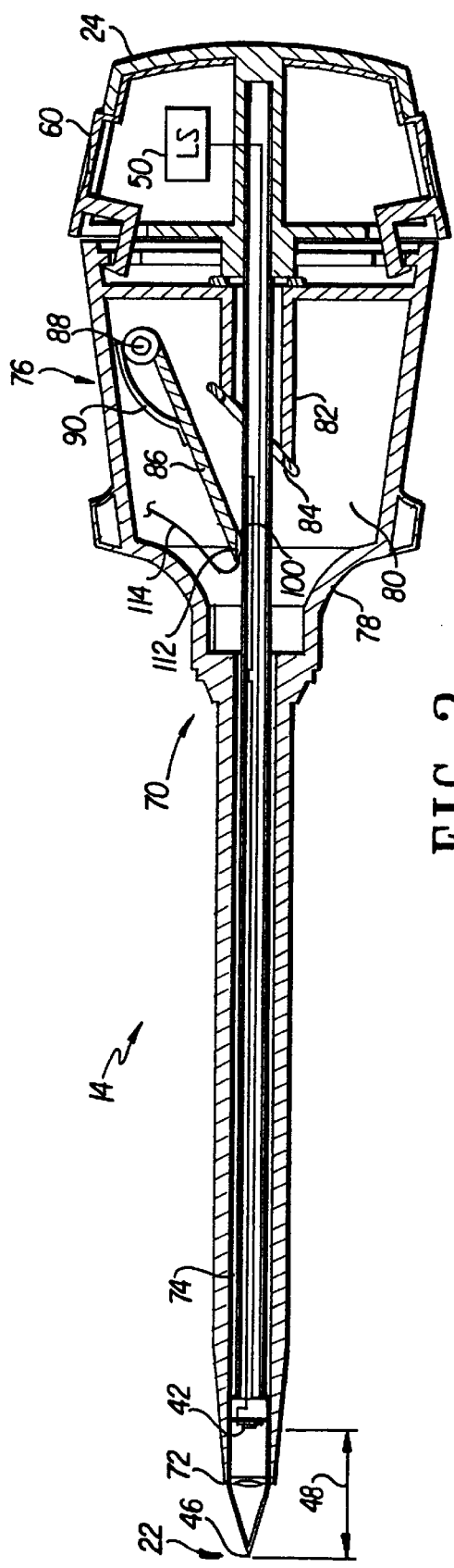
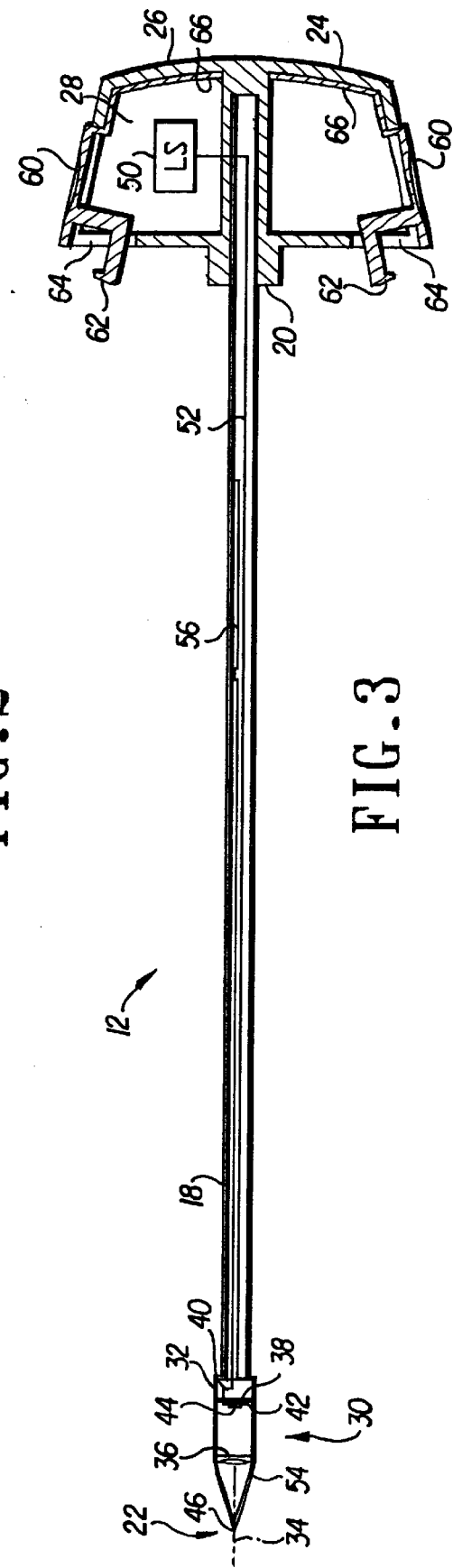
FIG._2
FIG._3

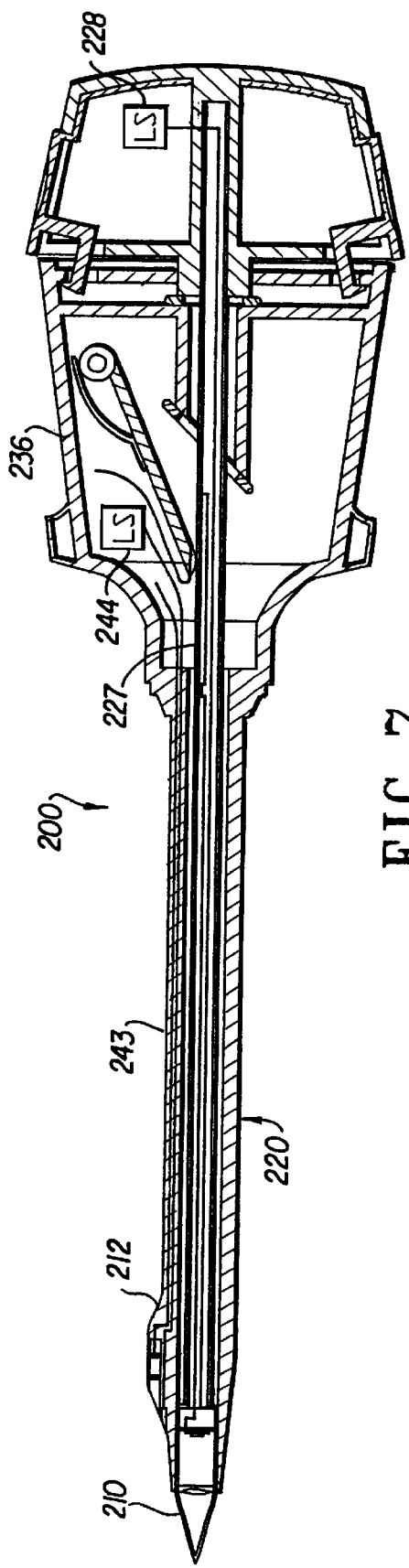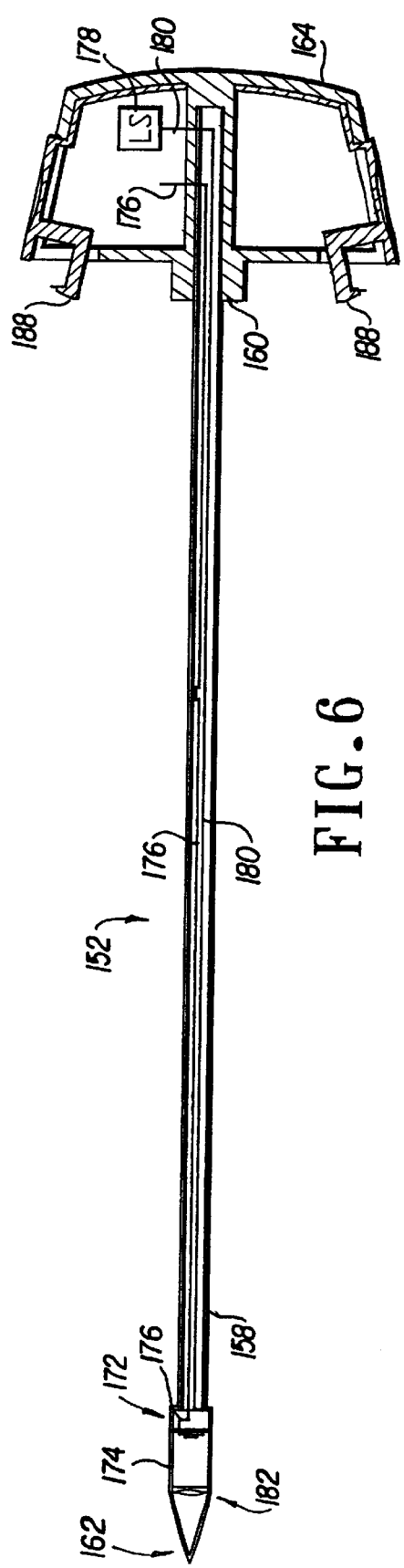

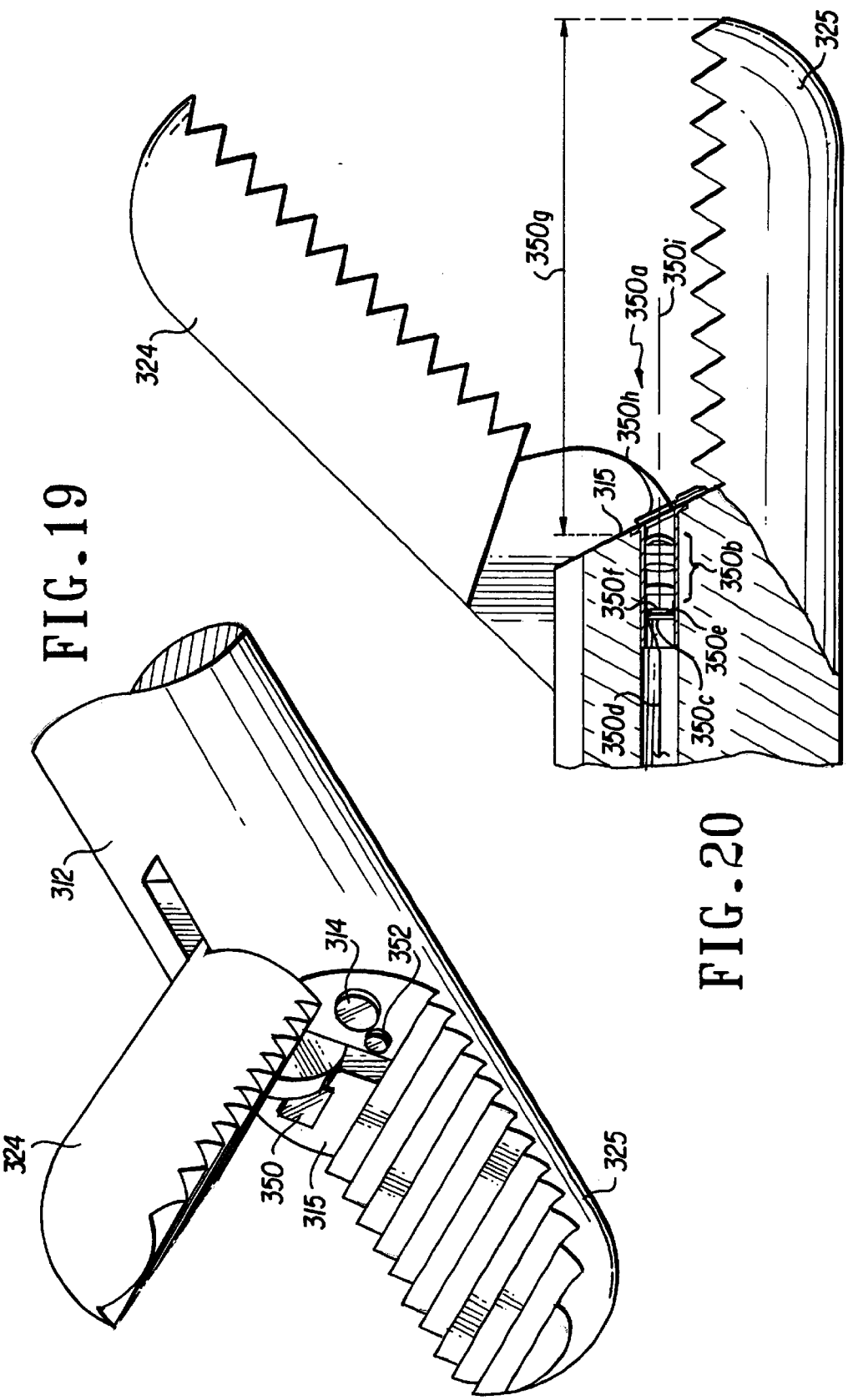

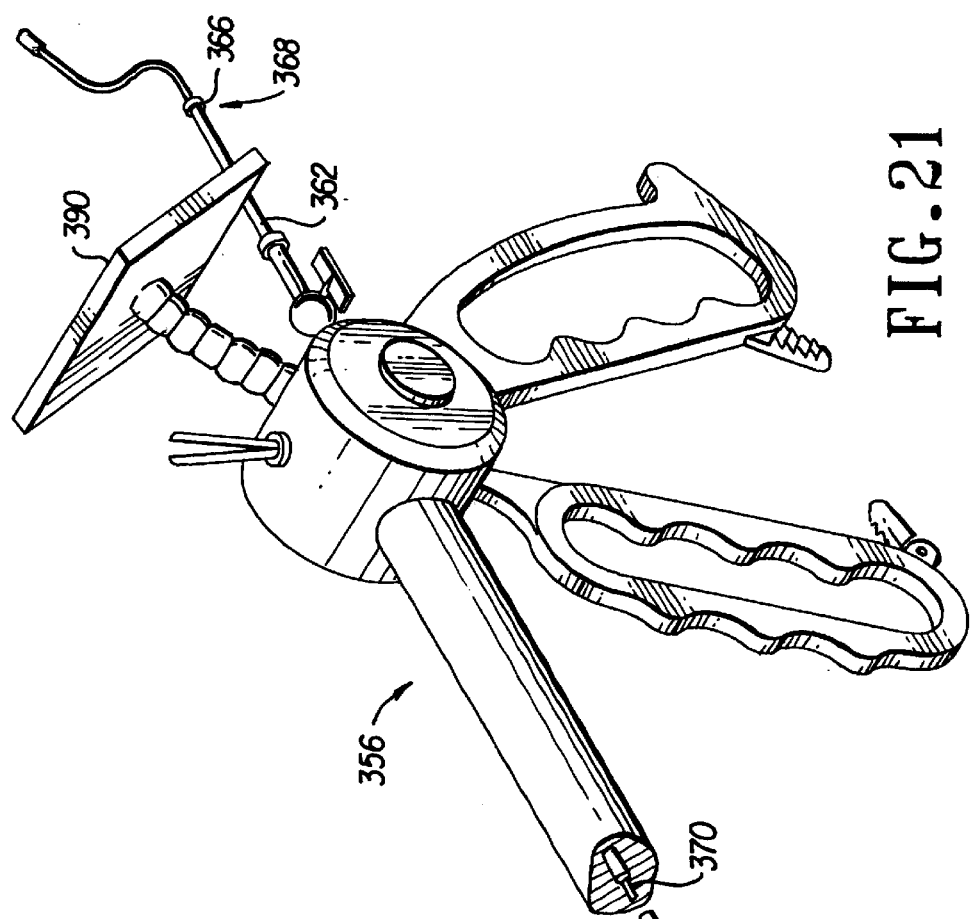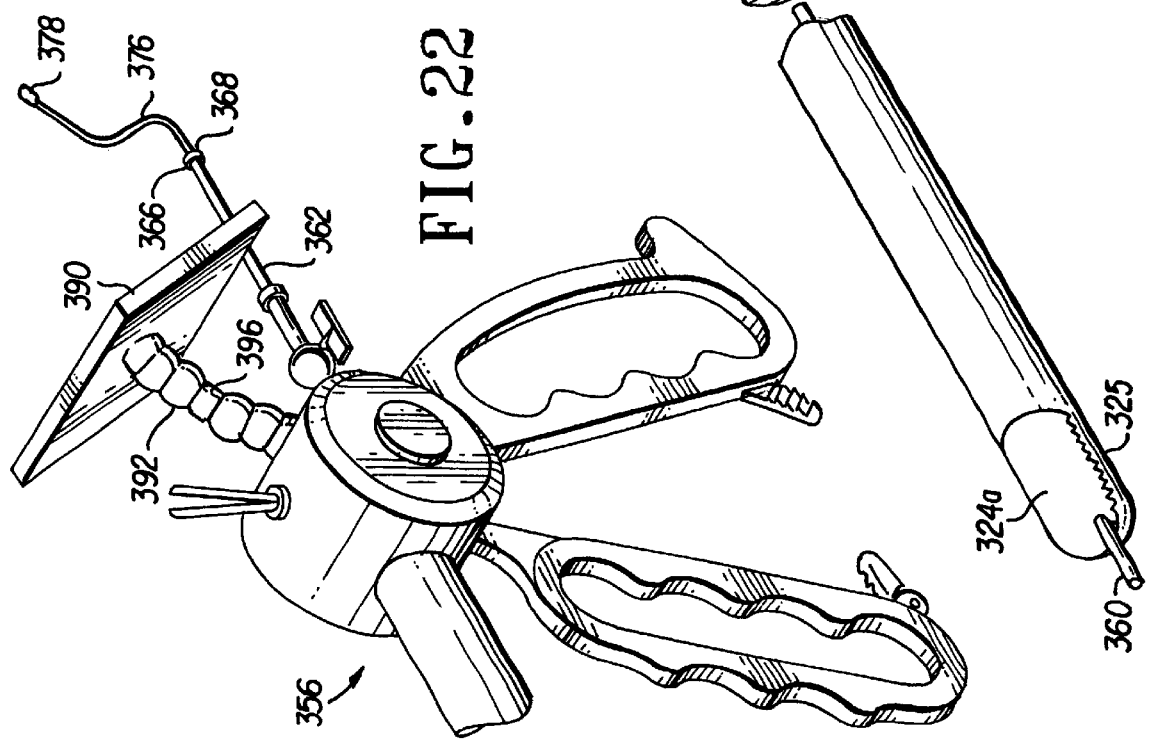

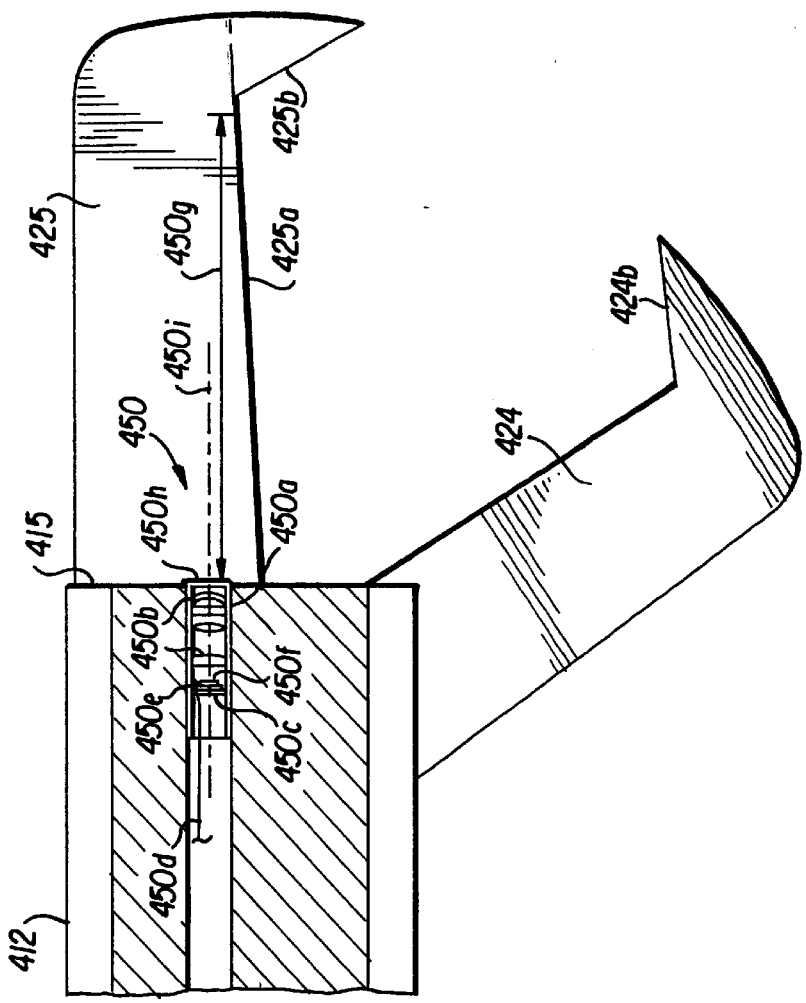
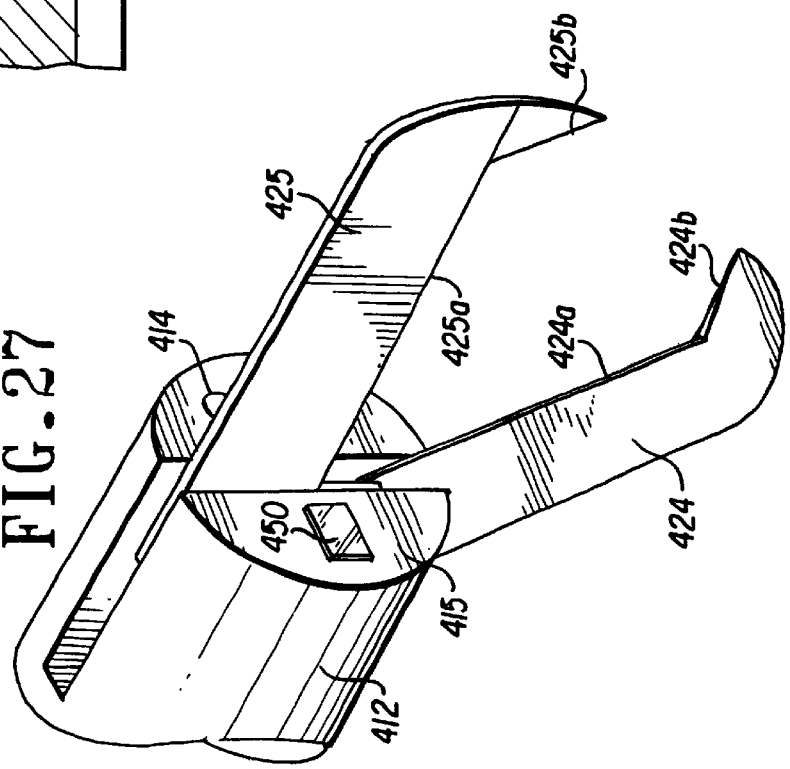

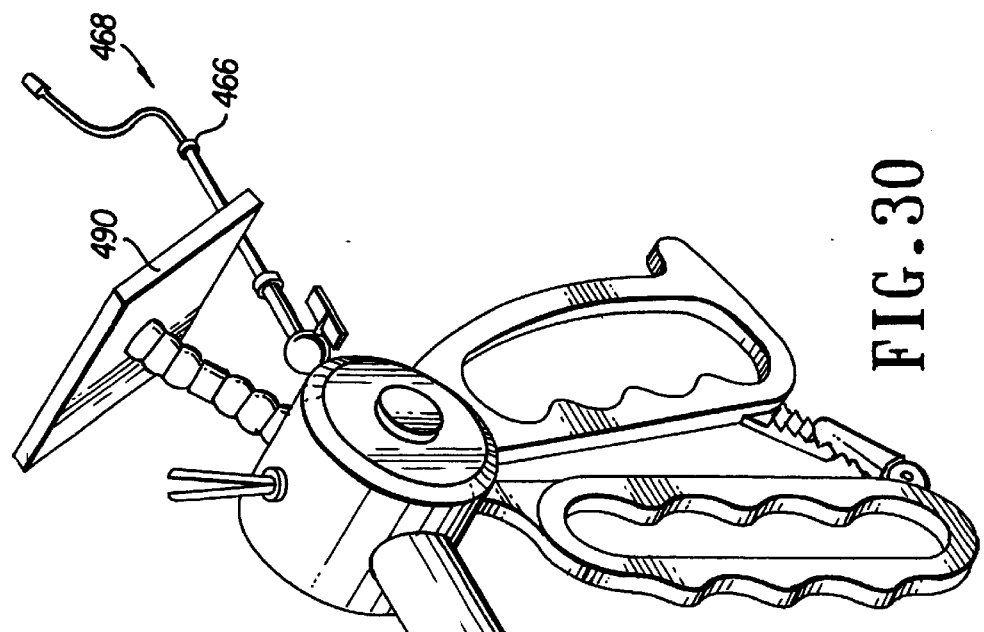
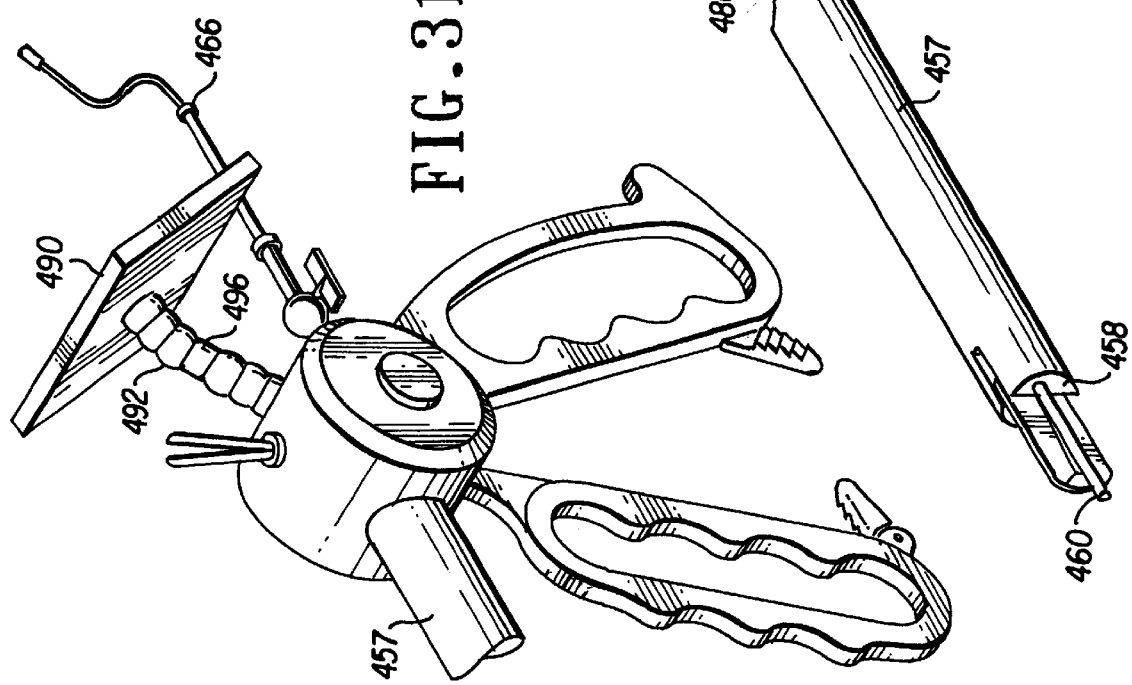

PENETRATING ENDOSCOPE AND ENDOSCOPIC SURGICAL INSTRUMENT WITH CMOS IMAGE SENSOR AND DISPLAY

RELATED APPLICATION DATA

This application is related to applicant's U.S. Pat. No. 5,632,717 and copending applications Ser. No. 08/847,187 and Ser. No. 08/847,254 (both filed May 1, 1997), as well as Ser. No. 08/366,285 (filed Dec. 29, 1994), Ser. No. 08/377,723 (filed Jan. 25, 1995), Ser. No. 08/401,002 (filed Mar. 9, 1995), Ser. No. 08/585,875 (filed Jan. 16, 1996), and Ser. No. 08/758,648 (filed Nov. 27,1996), the entire disclosures of which are incorporated herein by reference.

BACKGROUND OF THE INVENTION

This application claims benefit of U.S. application Ser. No. 60/085,243, filed May 13, 1998, which claim benefit of U.S. application Ser. No. 60/085,242, which claim benefit of U.S. application Ser. No. 60/093/069, filed Jul. 16, 1998.

1. Field of the Invention

The present invention pertains to endoscopes in general and, more particularly, to a penetrating endoscopic instrument with a solid-state image sensor for penetrating into anatomical tissue and an endoscopic surgical instrument carrying an endoscope with a solid-state image sensor.

2. Discussion of the Prior Art

Various procedures are accomplished in both open surgery and endoscopic surgery, and generally include multiple steps requiring various operating instruments. "Open surgery" refers to surgery wherein the surgeon gains access to the surgical site by a relatively large incision and "endoscopic surgery" refers to minimally invasive surgery wherein the surgeon gains access to the surgical site via one or more portals through which an endoscope is introduced to view the surgical site and through which instruments having "end effectors", such as forceps, cutters, needle holders, cauterizers, and the like, are introduced to the surgical site.

The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn, leaving the sleeve in place to form a portal in the cavity wall for the introduction of instruments such as endoscopes, scissors, forceps, needle holders and the like, into the anatomical cavity. The various end effectors at the distal end of the instrument are manipulated by the surgeon using controls disposed at the proximal end of the instrument while viewing the end effectors using the endoscope.

Endoscopes have included a variety of transducers such as vidicons (i.e., closed circuit television camera tubes) and solid-state Charge Coupled Devices (CCDs) for converting image light into electrical image signals for transmission to a viewing screen in the operating room (OR). CCD solid-state image sensors provide the benefits of small size and flexibility in image sensor placement, but are relatively difficult and expensive to implement in medical instruments, since CCD sensor signals require processing through complex and expensive ancillary equipment, if a usable image is to be displayed.

Endoscopic instruments, in general, also have been so expensive to use, sterilize and maintain that only surgeons in well-funded medical facilities have had access to instruments providing visualization in the body. There has been a long-felt need to move the site of medical care out of the OR to the hospital bed side or to an out-patient care facility. Endoscopic visualization could become an important component of patient-side care, were it available at a manageable price, and could be used for monitoring, as opposed to diagnosis, since endoscopic visualization could be performed daily or weekly, at bed side. If an economical, disposable alternative were available, endoscopic instruments for use at the bed side, in out-patient care, in ambulances or in the home could be provided for use in a wide variety of medical and dental applications.

Prior art endoscopes also suffer from many disadvantages when used in the procedures for which they are presently recommended. A major disadvantage of prior art endoscopes is that they cannot be used during penetration of anatomical tissue to view the anatomical tissue being penetrated (e.g. using a trocar penetrating member). Thus, it is difficult for a surgeon to know whether to alter the path of the perietrating member to avoid blood vessels and other types of anatomical tissue and organs. In an effort to overcome this disadvantage, a number of manufacturers have developed optical trocars such as the United States Surgical Corps Visiport™ trocar and the Ethicon Endosurgery's Optiview™ trocar, both of which employ a conventional elongated endoscope inserted into a lumen or cannula and providing visibility through a transparent trocar distal end. While the Visiport m and Optiview™ optical trocars do provide visibility during the penetrating step, they are still subject to the disadvantages associated with conventional endoscopic surgical procedures as outlined above and so are not useful in moving patient care out of expensive OR facilities and closer to the bed side.

SUMMARY OF THE INVENTION

A penetrating endoscope of the invention provides visualization of organ or tissue structures or foreign objects in a body. The penetrating endoscope includes an elongate penetrating member, a complementary metal oxide semiconductor (CMOS) image sensor and an objective lens. The elongate penetrating member has a longitudinal axis, a proximal end that is disposed externally and a sharp penetrating distal end that is adapted for insertion into the body by penetrating anatomical tissue. The CMOS image sensor is substantially planar and includes a plurality of pixels and a pixel signal processing circuit that generates a color image ready signal. The CMOS image sensor converts image light energy into electrical color image ready signal energy and transmits it out of the body. The color image ready signal is adapted for viewing on a color image display. The CMOS image sensor is carried on the elongate penetrating member adjacent the elongate penetrating member distal end.

The objective lens is carried on the elongate penetrating member distal end on an optical axis and focuses an image corresponding to an endoscope field of view at an image plane intersecting the optical axis. The CMOS image sensor is mounted with the CMOS image sensor pixels disposed substantially in the image plane and on the optical axis.

An alternative embodiment of the invention is an endoscope that provides visualization of organ or tissue structures or foreign objects in the body. The endoscope includes an elongate member but also has the longitudinal axis, the proximal end and the distal end as described above. The elongate member is adapted to be inserted through a portal into the body. Further, the endoscope includes the CMOS image sensor and the objective lens as described above.

Another alternative embodiment of the endoscope for providing visualization of organ or tissue structures or foreign objects in the body also includes the elements described above. Further, the endoscope includes at least one fixed focus objective lens element and a cutting end effector. The at least one fixed focus objective lens element has a depth of field with a selected minimum in-focus distance for an in-focus image at the image plane. The cutting end effector has a selected length substantially equal to or greater than the minimum in-focus distance.

The features and advantages of the present invention will become apparent upon consideration of the following detailed description of a specific embodiment thereof, particularly when taken in conjunction with the accompanying drawings, wherein like reference numerals in the various figures are utilized to designate like components.

BRIEF DESCRIPTION OF THE DRAWINGS

FIG. 1 is a side view in elevation of a penetrating endoscope with a CMOS image sensor and a display.

FIG. 2 is a cross section of the penetrating endoscope of FIG. 1.

FIG. 3 is a schematic illustration in partial cross section of the penetrating member included in the penetrating endoscope of FIG. 1.

FIG. 6 is a schematic illustration in partial cross section of the penetrating member included in the penetrating endoscope of FIG. 5.

FIG. 7 is a schematic illustration in partial cross section of an alternative embodiment of the penetrating endoscope of the present invention.

FIG. 8 is an enlarged schematic illustration in partial cross section of the distal end of the penetrating endoscope of FIG. 7.

FIG. 19 is an enlarged perspective illustration of the distal end of the surgical instrument of FIG. 18.

FIG. 20 is a partial cross section of the surgical instrument distal end of FIG. 19 showing a cross section of the sealed optics package taken in a plane parallel to the optical axis and perpendicular to the image plane.

FIG. 21 is a perspective view of an alternative embodiment of the surgical instrument.

FIG. 22 is an enlarged perspective illustration of the proximal end of the surgical instrument of FIG. 21, with the detachable image display.

FIG. 27 is an enlarged perspective illustration of the distal end left side of the surgical instrument of FIG. 1.

FIG. 28 is a partial cross section of the surgical instrument distal end of FIG. 27 showing a cross section of the sealed optics package taken in a plane parallel to the optical axis and perpendicular to the image plane.

FIG. 30 is a perspective view of an alternative embodiment of the surgical instrument having a separate insertable endoscope.

FIG. 31 is an enlarged perspective illustration of the proximal end of the surgical instrument of FIG. 30, with the detachable image display.

DESCRIPTION OF THE EXEMPLARY EMBODIMENTS

Figure 4:
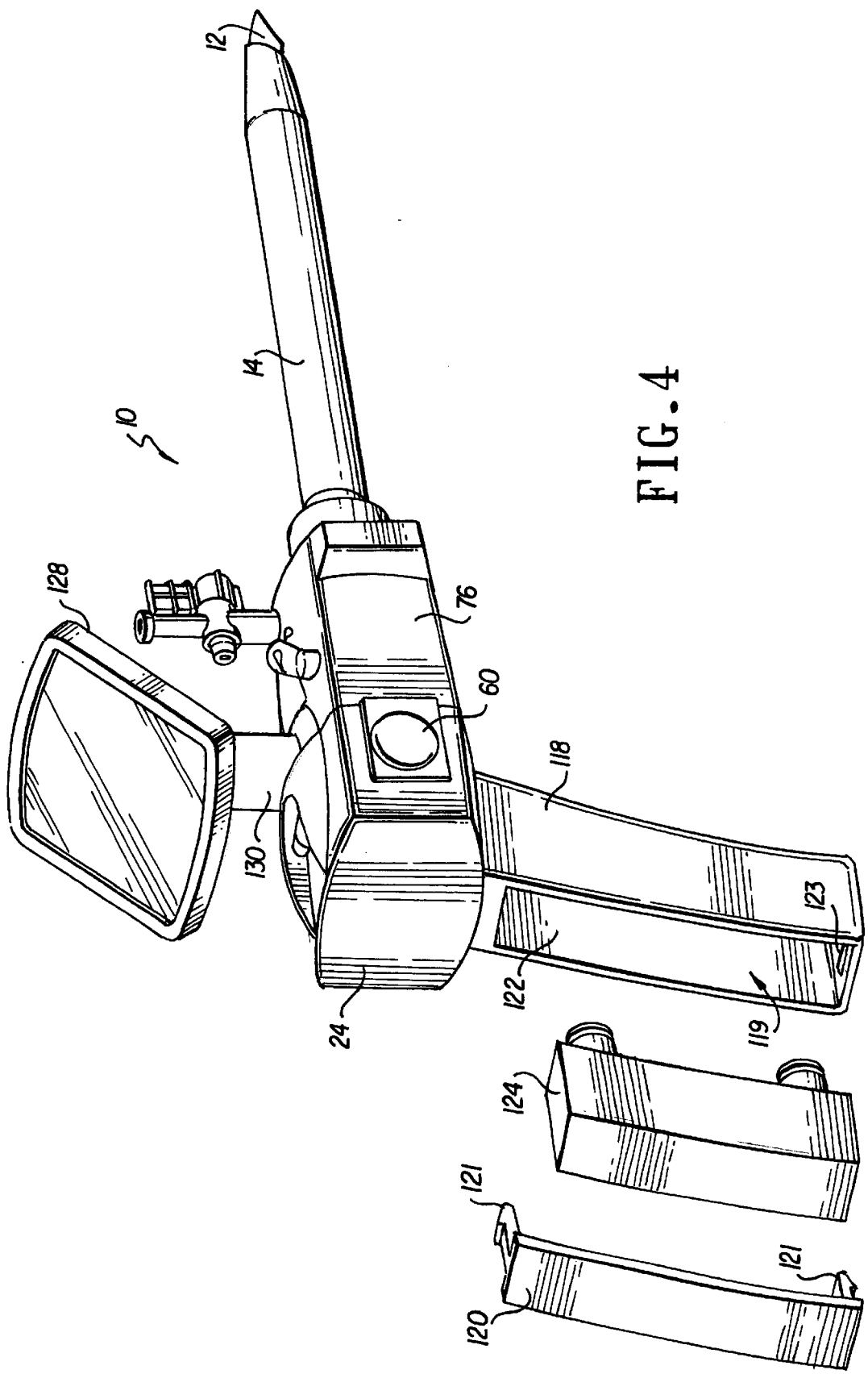
FIG. 4 is a perspective view of the penetrating endoscope of FIG. 1.

A penetrating endoscope 10 according to the present invention, as illustrated in FIGS. 1–3 includes a penetrating member 12 slidably received within a portal sleeve or cannula 14. FIG. 2 is a schematic illustration in partial cross section of the penetrating member 12 slidably received within portal sleeve 14. FIG. 3 is a schematic illustration in partial cross section illustrating the internal workings of the penetrating member 12 which includes an elongate tube-like body 18 having a proximal end 20 and a sharp penetrating distal end 22. A penetrating member housing 24 is carried on the penetrating member elongate body proximal end 20 and includes a housing wall 26 enclosing a housing cavity 28. The penetrating member sharp penetrating distal end 22 is substantially transparent and is incorporated in a sealed optics package 32 having a complementary metal oxide semiconductor (CMOS) image sensor 30 disposed along an optical axis 34 with a transparent sharp penetrating tip 46. One or more objective lens elements 36 are also disposed along optical axis 34 within sealed optics package 32. CMOS image sensor 30 includes a CMOS image sensing chip 42 disposed in a plane intersecting and transverse to optical axis 34. CMOS image sensing chip 42 is substantially planar and is electrically connected to and carried by a substantially planar printed circuit board 38 having electrical connections 40 for carrying image signals proximally out of the body. CMOS image sensing chip 42 includes a plurality of picture elements or pixels in a rectangular grid, 640 pixels by 480 pixels. By CMOS image sensor is meant a solid-state image sensor fabricated using the well known, economical complementary metal oxide semiconductor (CMOS) process, i.e., the integrated circuit (IC) fabrication technology usually combining either or both of enhancement mode N-channel (NMOS) and enhancement mode P-channel (PMOS) field effective transistors (FETs), preferably on a single substrate to form logic gates, memory cells, image sensor pixels, or transistors along with a microprocessor or the like and preferably incorporates, on a single substrate (or chip) image signal processing, memory, and data transmission circuitry to generate image ready signals and transfer the image ready signals out of the body over electrical connection 40. By image ready signal is meant a signal processed and adapted to be readily displayed on an image display. Any of several standards for image signal processing and transmission are suitable; for example, signal processing circuits on CMOS image sensing chip 42 can be selected to convert periodically sampled individual pixel voltage (or current) levels into a National Television System Committee (NTSC) image signal for transmission out of the body and display on an NTSC compatible image display (e.g., a television). The CMOS image sensor 30 preferably has a plurality of MOS pixel circuits integrated onto chip 42 proximate a Red-Green-Blue (RGB) mosaic color filter panel 44 (as shown in FIG. 3) constituted by a mosaic arrangement of Red-Green-Blue color filters, thus permitting any single pixel to receive either red, green or blue filtered light energy. The color mosaic filter panel 44 is disposed on the optical axis 34 of sealed optics package 32, ahead of the transverse imaging surface of the CMOS chip 42. The pixels receiving red, green and blue light generate, respectively, red, green and blue pixel light intensity values for color image ready signal generation. The objective lens elements 36 comprising the objective lens in sealed optics package 32 are preferably fixed in position providing a fixed depth of field at an image plane substantially coplanar or coincident with the plane containing the pixels of CMOS image sensing chip 42. Optical axis 34 (shown as a dotted line through sealed optics package 32 in FIG. 3) extends linearly from the transparent penetrating tip 46 proximally to the image sensing chip 42 being disposed transverse thereto, in the image plane. The objective lens comprised of lens elements 36 focuses an image corresponding to the endoscope field of view at the image plane intersecting and transverse to the optical axis 34; the objective lens is preferably fixed focused, meaning that a fixed depth of field is provided having a selected minimum in focus distance 48 (as shown in FIG. 2). Transparent penetrating tip 46 is therefore disposed at an axial length beyond the image plane containing CMOS image sensing chip 42; the axial length 48 is substantially equal to or greater than the minimum in focus distance such that the penetrating member transparent tip 46 is in focus at the image plane containing image sensing tip 42 and the depth of field for sealed optics package 32 renders everything at or beyond transparent tip 46 in focus at the image plane coplanar with CMOS image sensing chip 42.

In the embodiment of FIG. 3, penetrating member 12 includes a light source 50 disposed within the penetrating member housing cavity 28 and connected via an optical wave guide 52 for propagating visible light to a distally aimed illumination emitter 54 to illuminate substantially all of the field of view of sealed optics package 32. Optionally, illumination emitter 54 includes a light emitting diode or other light generator energized by conductors carried on the penetrating member elongate body 18.

Penetrating member elongate body 18 includes, at a medial location, a conforming sliding electrical contact 56 electrically connected to the image sensor printed circuit board electrical connection 40 via one or more electrical conductors carried within the elongate body 18. Sliding electrical contact 56 preferably includes a plurality of axially aligned thin strips of conductive material such as gold or copper in a parallel array disposed radially around penetrating member elongate body 18 and carries image ready signal energy proximally, out of the body.

As best seen in FIG. 3, penetrating member housing 24 includes first and second buttons or levers 60 carrying and actuating first and second latches or tab members 62 movably mounted in first and second slots 64 defined in the penetrating member housing wall 26. Each lever 60 and tab member 62 is resiliently biased into the outward position (as shown in FIG. 3) by a leaf spring 66 carried on the penetrating member housing wall 26. Penetrating member 12 can be used with a conventional trocar cannula such as the Ethicon® ENDOPATH® trocar cannula which includes apertures in the cannula housing for receiving penetrating member tab members 52. An Ethicon trocar having a transparent cannula is disclosed in U.S. Pat. No. 5,256,149 (to Banik et al), the entire disclosure of which is incorporated herein by reference.

As best seen in FIG. 2, portal sleeve 14 is preferably an elongate, rigid, distally tapered tubular, sleeve including a tapered open distal end 72 and a proximal end 70 in communication therewith via an open lumen 74. Portal sleeve 14 is generally an elongate tubular member symmetrical about a longitudinal axis and carries, on portal sleeve proximate end 70, a portal sleeve housing 76 having a portal sleeve housing exterior wall 78 enclosing a portal sleeve housing interior volume 80. Portal sleeve housing interior volume 80 includes an inwardly projecting tubular passage 82 terminating distally in a valve seat 84 which can be sealably engaged with a substantially planar flapper valve 86 carried by and pivoting about a flapper valve pivot pin 88. Flapper valve 86 is spring biased toward tubular passage valve seat 84 by a resilient leaf spring member 90. Flapper valve 86 includes, preferably, a plurality of electrical contacts 100 aligned in a parallel array on flapper valve distal end 112 for cooperative sliding engagement with the penetrating member sliding electrical contacts 56 arrayed on the penetrating member elongate body 18 when the penetrating member is received within the portal sleeve, as shown in FIG. 2. Flapper valve contacts 100 are preferably connected to one ore more electrical conductors 114 for transmitting or carrying the image signal.

Turning now to FIG. 1 and FIG. 4, a hollow portal sleeve housing handle 118 projects transversely from and is carried by the portal sleeve housing 76 and includes a rectangular access opening 119a that receives handle access cover 120.

Access cover 120 is detachably attached to portal sleeve housing handle 118 and is retained in place by first and second projecting resilient tabs 121 which are received within the hollow portal sleeve housing handle interior and snap-fit into cooperating notches 123 in the housing side wall 122 interior surfaces. The hollow portal sleeve handle interior volume receives a removable (and preferably disposable) power cell or battery 124 having first and second electrical contacts; battery 124 provides power for energizing all of the electrical and electronics circuitry in penetrating endoscope 10. In particular, a voltage supply bus is provided using electrical conductors within portal sleeve housing handle 118 and portal sleeve housing 76 for providing electrical energy to the CMOS image sensor 30, the data transmission circuits and the solid state display 128.

Display 128 is a substantially planar solid state video monitor receiving image ready signals from CMOS image sensor 30 and providing a readily visible display of objects in the field of view of the image sensor. Display 128 is carried atop an adjustable or repositionable mount or stalk 130 affixed upon portal sleeve housing 76. Adjustable mount 130 has first and second position adjustment control knobs (as best seen in FIG. 1) for adjusting the angular orientation of display 128, thereby permitting the surgeon to aim the display for convenient observation. Display 128 is preferably implemented as a Liquid crystal display, a CMOS solid state display, a flat-panel plasma display or any other compact, relatively high definition type of display and is preferably detachably mounted and includes detachable electrical connectors for convenient removal and reattachment, thereby permitting the portal sleeve housing to be discarded after use.

Figure 5:
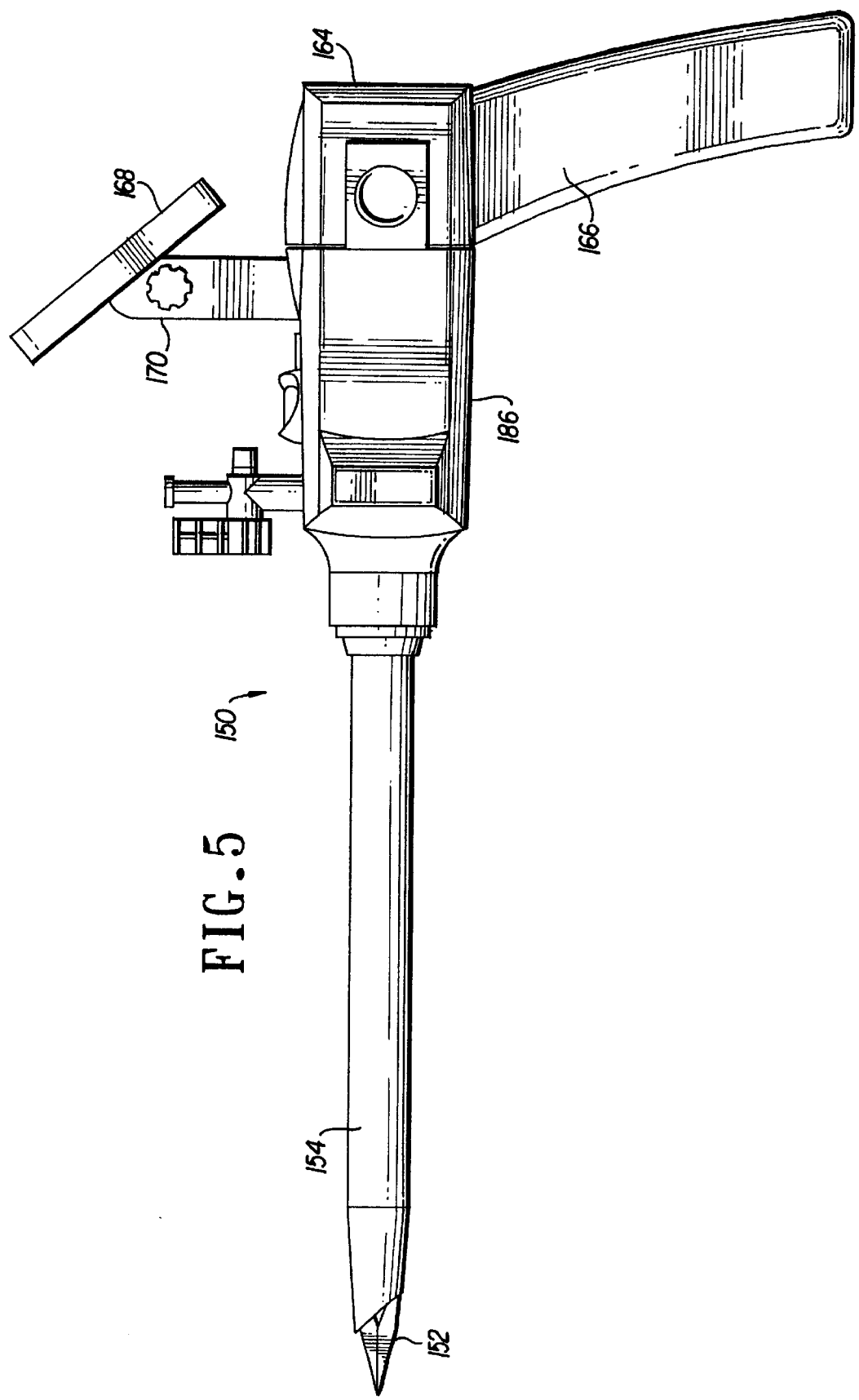
FIG. 5 is a left side view, in elevation, of an alternative embodiment of the penetrating endoscope of the present invention.

Turning now to FIG. 5, an alternative embodiment includes a penetrating endoscope 150 having a display mounted on the penetrating member housing instead of the portal sleeve housing. As shown in FIGS. 5 and 6, penetrating endoscope 150 includes a penetrating member 152 and portal sleeve 154. Penetrating member 152 includes a penetrating member elongate body 158 having a sharp distal end 162 opposite a proximal end 160. Proximal end 160 carries a penetrating member housing 164 which includes a transversely projecting penetrating member housing handle 166 and an adjustably mounted penetrating housing display 168 affixed atop an adjustable display mount 170. Penetrating member 152 includes a CMOS image sensor 172 incorporated into a sealed optics package 174 having a transparent penetrating distal tip. An electrical connection 176 preferably including a plurality of conductors connects CMOS image sensor 172 with display 168; electrical connection 176 terminates distally at the CMOS image sensor printed circuit board and is preferably contained within the interior of penetrating member elongate body 158 and terminates proximally within penetrating member housing 164 in a connection to display 168 thereby transmitting image signal energy proximally and out of the body to the display. Penetrating member 152 also includes a light source 178 preferably contained within penetrating member housing 164 and generating light to be transmitted distally over optical wave guide 180 to an illumination emitter 182. Illumination emitter 182 is advantageously contained within a sidewall of sealed optics package 174 and projects a distal beam of illumination which is at least coextensive with the field of view of CMOS image sensor 172.

Portal sleeve 154 is terminated proximally at a portal sleeve housing 186 which retains penetrating member housing 164 by operation of the biased tab numbers 188, as above.

Penetrating endoscope 150 of FIGS. 5 and 6 may be grasped by handle 166 and after the penetrating step, may be separated by actuation of bias tab members 188 thereby allowing the surgeon to withdraw the entire penetrating member 152 from portal sleeve 154 thereby removing the CMOS image sensor 172 and display 168, both of which are carried by the removable penetrating member 152.

Yet another embodiment of the penetrating endoscope of the present invention is illustrated in FIG. 7 and includes first and second CMOS image sensors. A first CMOS image sensor is incorporated in the penetrating distal tip of the penetrating member and a second CMOS image sensor is incorporated into the portal sleeve in close proximity to the tapered open end. FIG. 8 shows the distal ends of penetrating member 210 and the portal sleeve 212.

As shown in FIG. 7, penetrating endoscope 200 has a configuration very similar to that discussed above and includes a penetrating member 210 disposed within a portal sleeve 212 where the penetrating member includes an elongate body 214 having a proximal end 216 opposite a sharp distal end 218. A penetrating member housing 220 is carried on the proximal end of elongate body 214. The penetrating endoscope 200 of FIGS. 7 and 8 includes a penetrating member CMOS image sensor 224 disposed within the penetrating member sharp distal end 218 as well as a second portal sleeve mounted CMOS image sensor 238 disposed near the open distal end of portal sleeve 212 (and as best seen in the enlarged view of the instrument distal end shown in FIG. 8.) Penetrating member CMOS image sensor 222 is enclosed within a sealed optics package 224 and is connected with a penetrating member image sensor electrical connection 226 including a plurality of electrical conductors trained distally within penetrating member elongate body 214 to a sliding contact 227 adapted to make a sliding electrical connection with a flapper valve sliding contact 229 for transmitting image signals from the penetrating member image sensor 222 proximally for display. A penetrating member light source 228 is disposed within penetrating member housing 220 and generates light or illumination conducted distally over a penetrating member optical wave guide 230 for transmitting illumination distally to the penetrating member illumination emitter 232 best seen in FIG. 8.

Portal sleeve 212 is terminated proximally in the hollow portal sleeve housing 236 upon which is mounted an adjustable display similar to that shown in FIGS. 1 and 4. Portal sleeve housing 236 also includes an image signal control module (not shown) responsive to the presence of penetrating member 210 for controlling the selection of which image signal to display, that from penetrating member CMOS image sensor 222 or, alternatively, from that portal sleeve CMOS image sensor 238. Alternatively, the image signal control module may be adjusted to display images from both image sensors on the portal sleeve housing display.

Portal sleeve CMOS image sensor 238 is preferably reduced in size as compared to the penetrating member image sensor 222 and readily fits in a transversely projecting blister, thereby permitting visualization from the portal sleeve without substantially reducing the ease of insertion of the penetrating endoscope 200. Portal sleeve image sensor 238 is integrated into a sealed optics package 240 and is connection via an electrical connection 242 running proximally into portal sleeve housing 236 via wires embedded in the portal sleeve sidewall 243. A portal sleeve light source 244 is disposed within portal sleeve housing 236 and light generated in light source 244 is propagated distally via optical wave guides 246 to a portal sleeve illumination emitter 248, best seen in the enlarged view of FIG. 8, and illuminates substantially all of the field of view of portal sleeve CMOS image sensor 238.

In use, the penetrating endoscope of the present invention provides the surgeon with a view of tissue or organ structures during the penetrating steps and, optionally, a view of organ structures and foreign objects inside the body after penetration.

Figure 9:
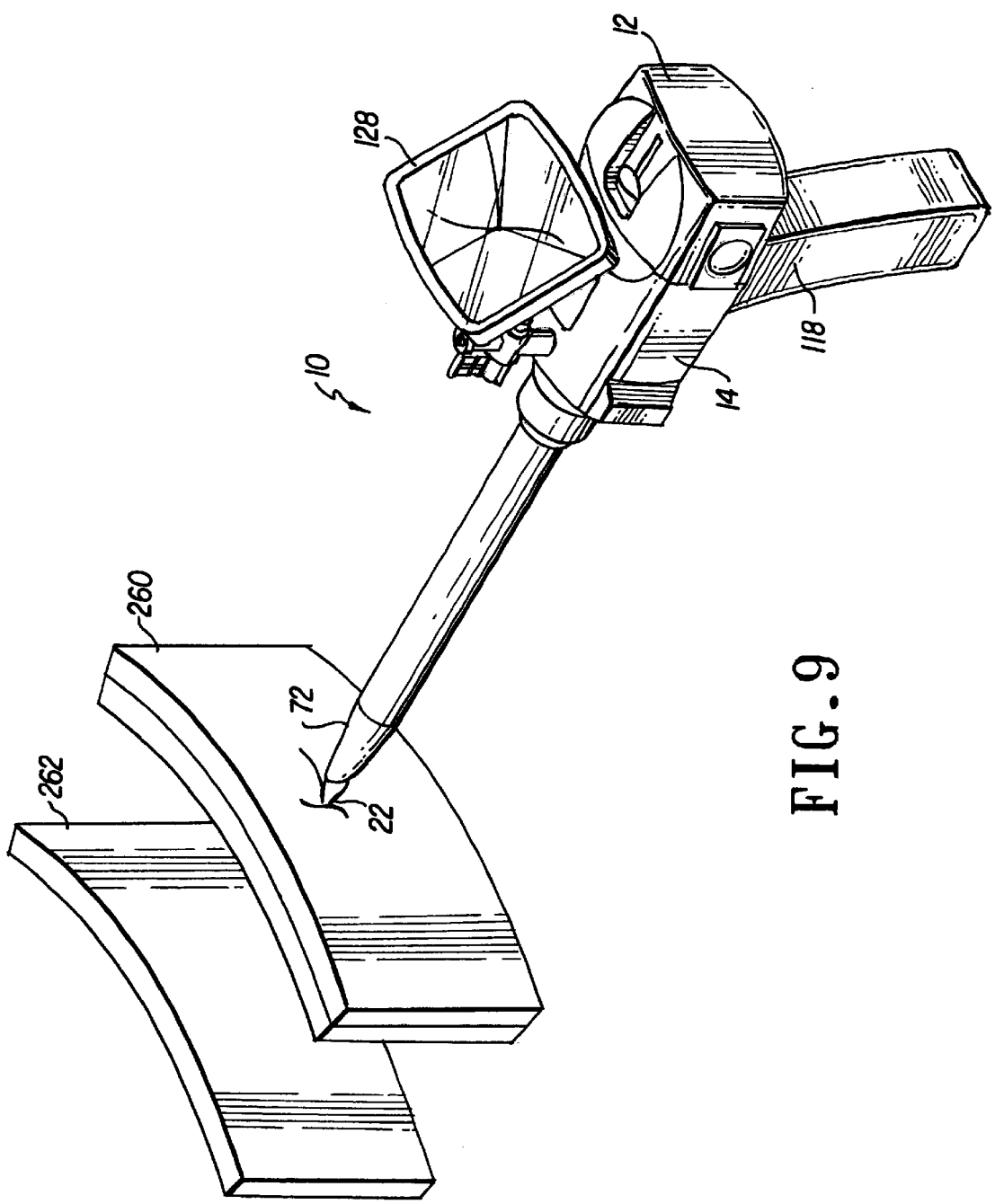
FIG. 9 is a perspective illustration of the penetrating endoscope of FIG. 1 in use, before penetrating an outer tissue wall.
Figure 10:
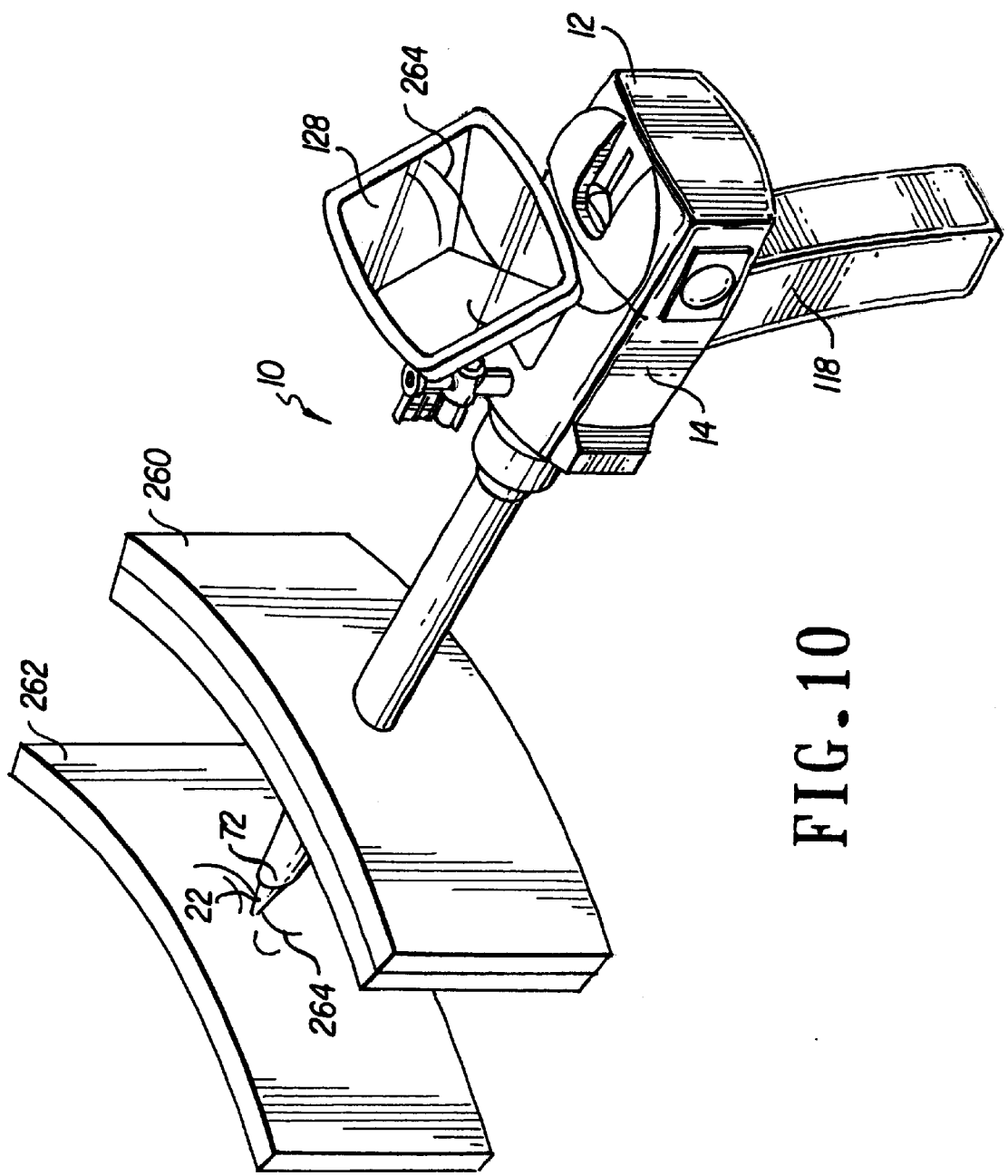
FIG. 10 is a perspective illustration of the penetrating endoscope of FIG. 9 in use, after penetrating an outer tissue wall.
Figure 11:
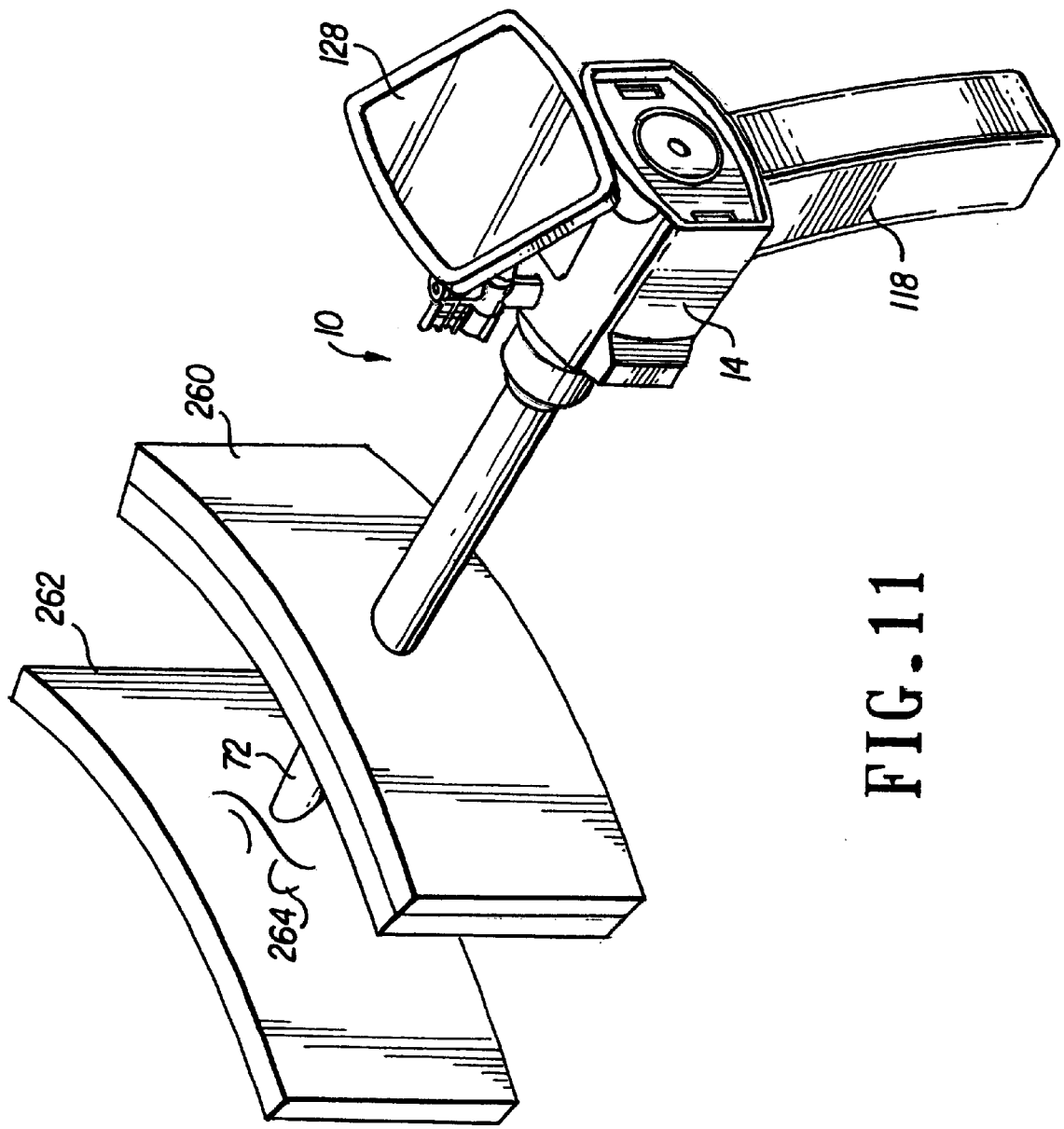
FIG. 11 is a perspective illustration of the penetrating endoscope of FIG. 9 in use, after removal of the penetrating member.

Turning now to FIGS. 9, 10 and 11, penetrating endoscope 10 is shown penetrating an outer tissue wall 260 to provide visualization of an interior organ wall 262 bearing a plurality of interior organ wall surface features 264. As shown in FIG. 9, penetrating endoscope 10 is positioned against outer tissue wall 260 and sharp penetrating distal end 22 is positioned at the desired puncture site. Display 128 shows the image observed via CMOS image sensor during the puncturing step. As shown in FIG. 10, the surgeon applies a forward thrusting force to penetrating endoscope 10 using transverse projecting handle 118 thereby puncturing or penetrating through outer tissue wall 260 into the cavity between outer tissue wall 260 and interior organ wall 262; sharp penetrating distal end 22 is disposed in a space between outer tissue wall 260 and interior organ wall 262 thereby permitting the surgeon to view the interior organ wall surface features 264 as perceived from the point of view of the CMOS image sensor 30 disposed within penetrating member distal end 22. Display 128 shows surface features 264, permitting the surgeon to identify interior organ wall 262 by recognition of surface features 264. After the insertion step, the surgeon removes penetrating member 12 from portal sleeve 14 thereby removing CMOS image sensor 30, whereupon display 128 of penetrating endoscope 10 conveys no further information to the surgeon.

Figure 12:
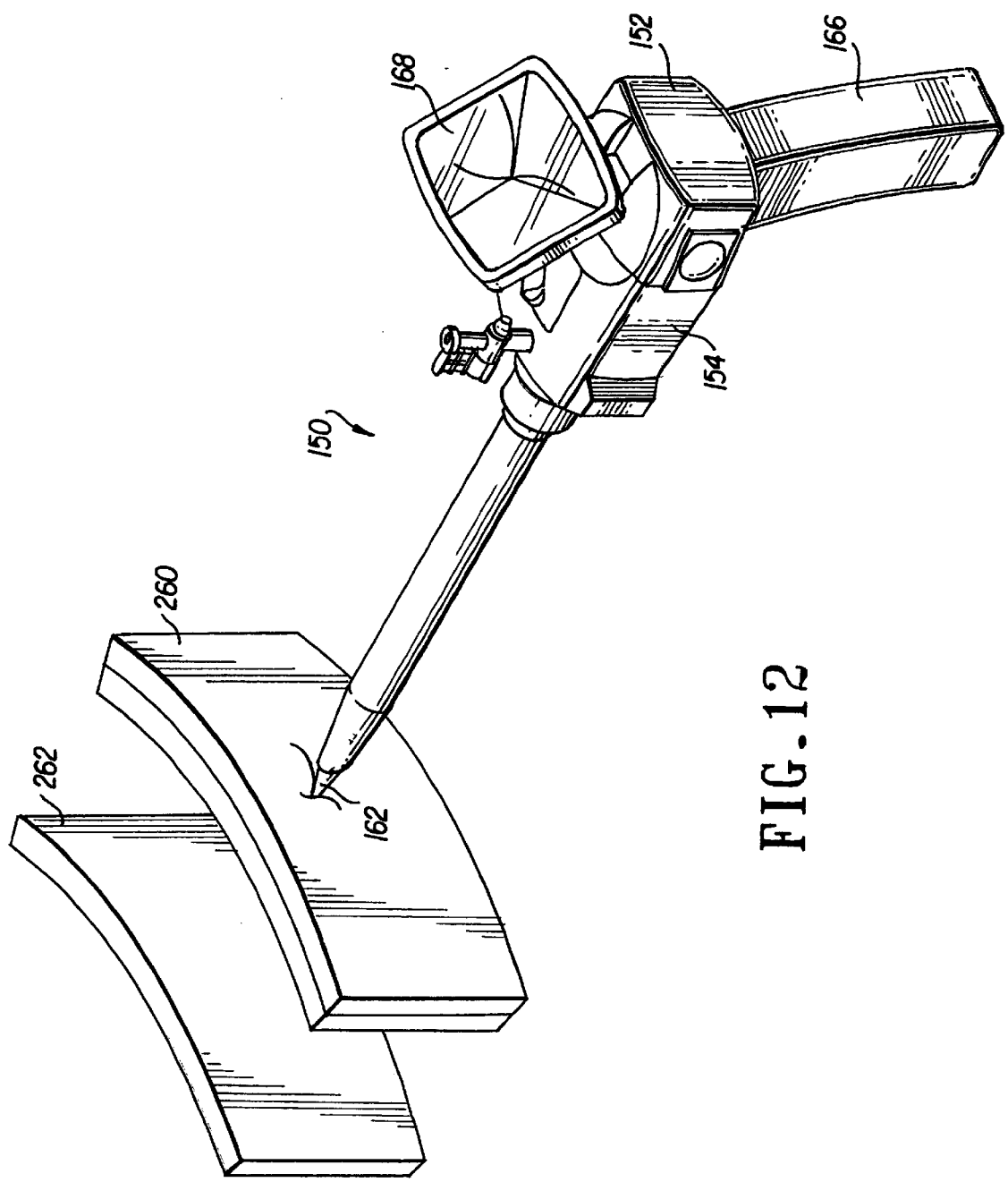
FIG. 12 is a perspective illustration of the penetrating endoscope of FIG. 5 in use, before penetrating an outer tissue wall.
Figure 13:
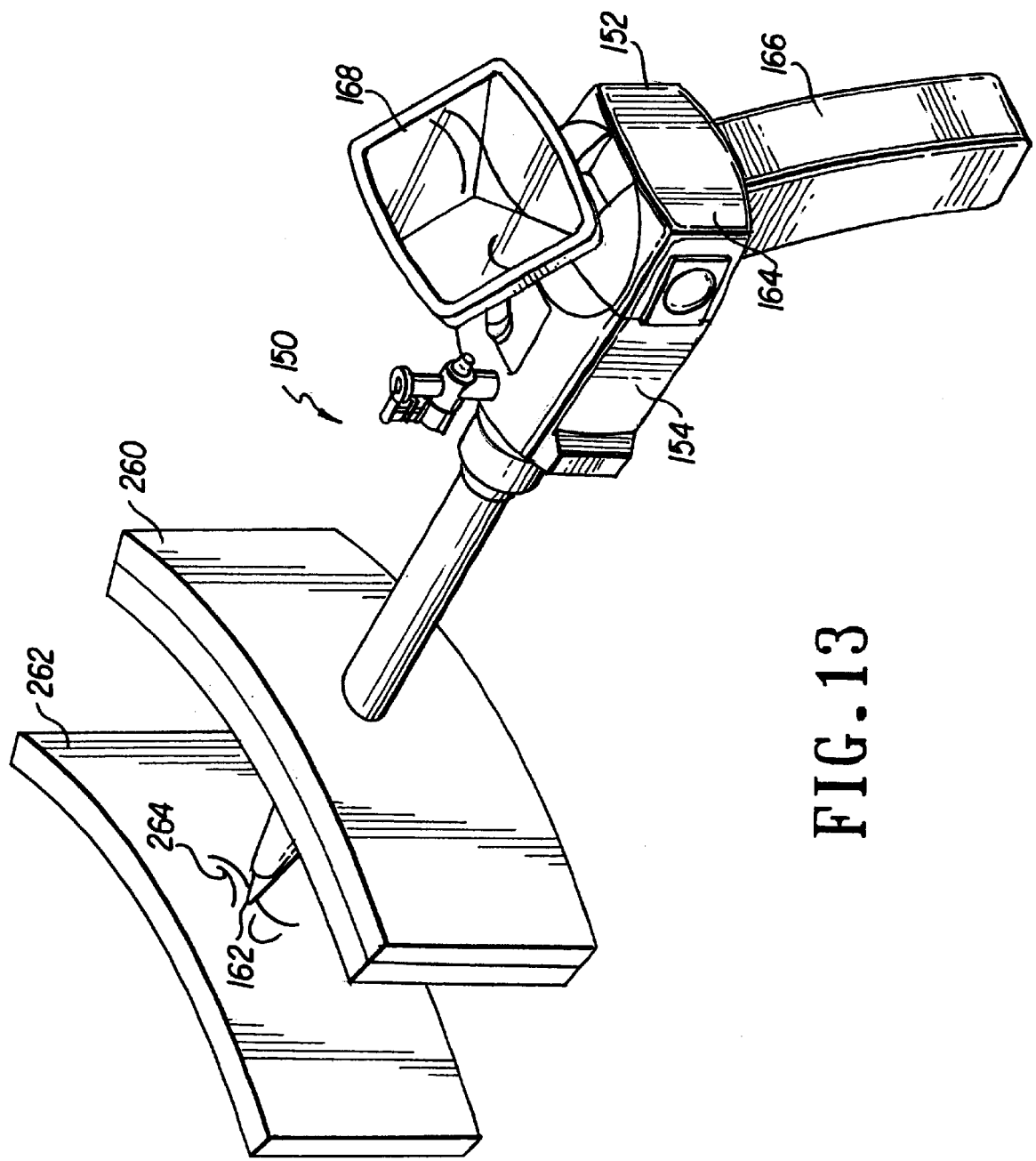
FIG. 13 is a perspective illustration of the penetrating endoscope of FIG. 12 in use, after penetrating an outer tissue wall.
Figure 14:
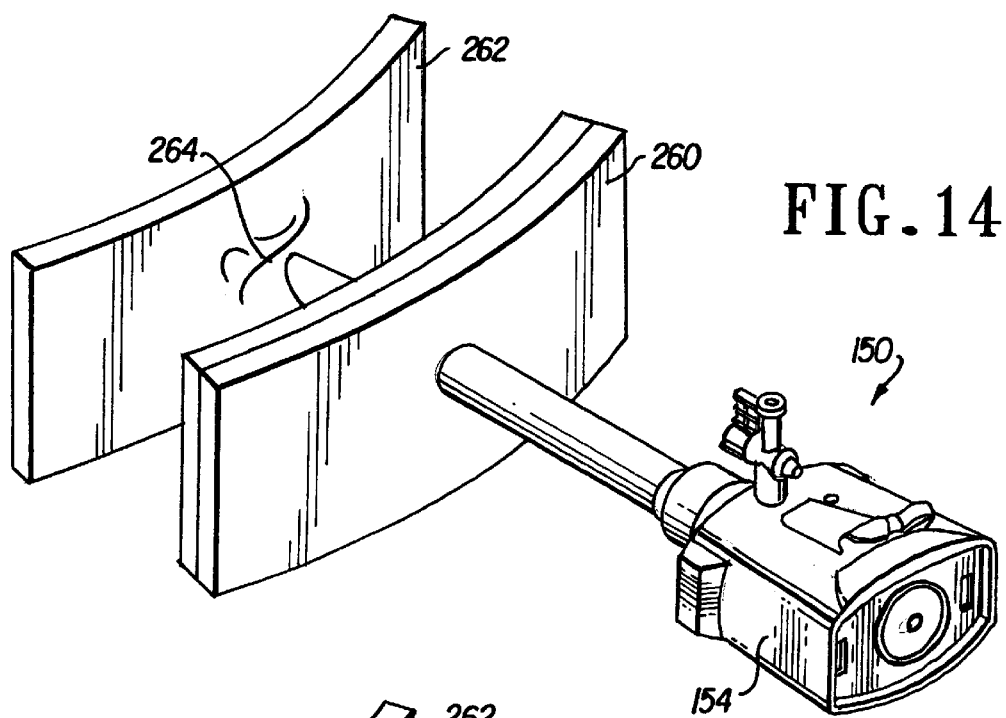
FIG. 14 is a perspective illustration of the penetrating endoscope of FIG. 12 in use, after removal of the penetrating member.

The alternative embodiment of the penetrating endoscope 150 (of FIG. 5), is used as shown in FIGS. 12,13 and 14. A surgeon first positions penetrating endoscope 150 with sharp distal end 162 (and the included CMOS image sensor 172) against an outer tissue wall 260 at the selected penetration site. As shown in FIG. 13, the surgeon applies a forward thrusting force to penetrating endoscope 150 using transverse projecting handle 166 thereby puncturing or penetrating through outer tissue wall 260 into the cavity between outer tissue wall 260 and interior organ wall 262 whereupon the CMOS image sensor 172 provides a view of interior organ wall surface features 264 on the adjustable display 168.

Once the penetrating step is complete, the surgeon may detach penetrating member housing 164 from portal sleeve housing 154 and remove penetrating member 152 from within the portal sleeve 154, thereby deactivating display 168 and providing an access port for conventional endoscopic surgery. The penetrating member 152 having image sensor 172 and display 168 may then be set aside for sterilization, if desired. Penetrating endoscope 150 optionally combines a reusable, sterilizable penetrating member 152 with a disposable portal sleeve (available from Ethicon Endo-Surgery™ and others).

Figure 17:
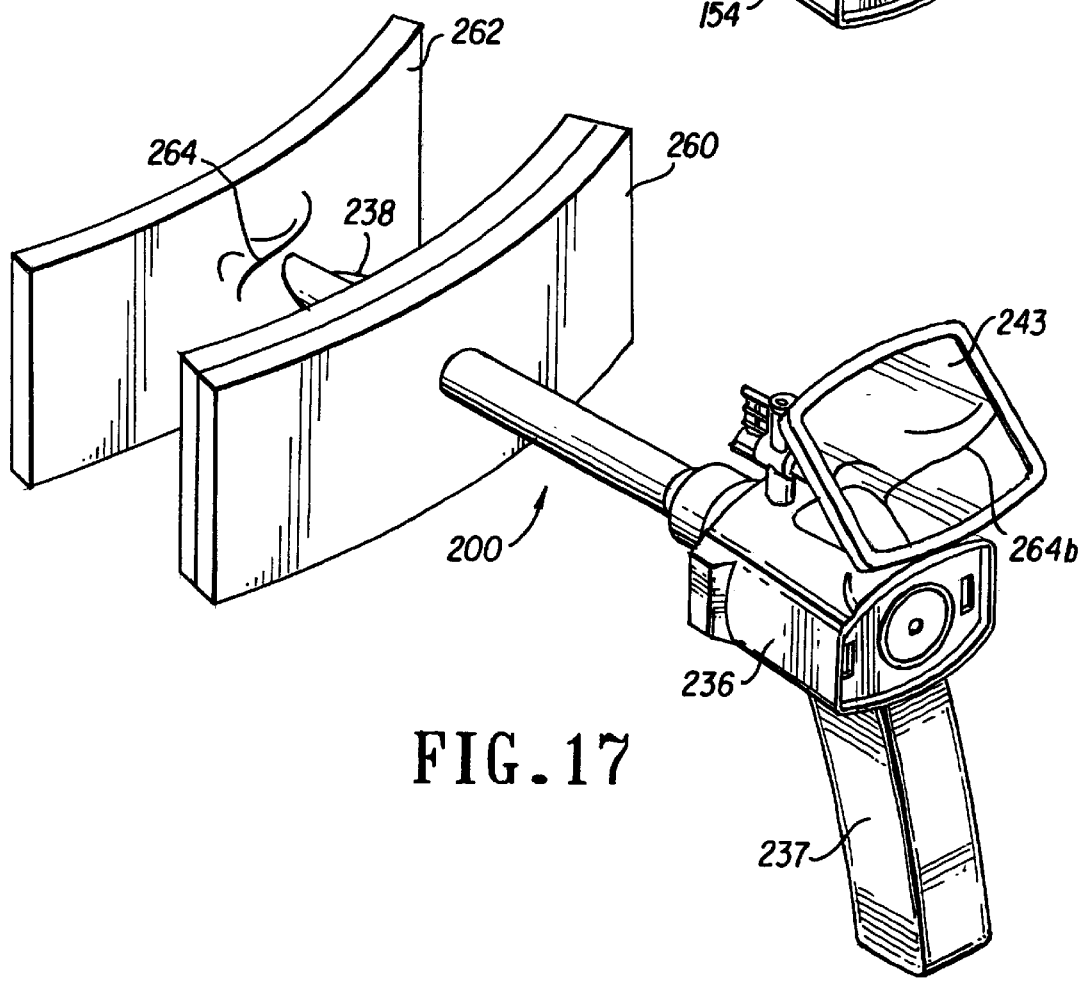
FIG. 17 is a perspective illustration of the penetrating endoscope of FIG. 15 in use, after removal of the penetrating member.
Figure 15:
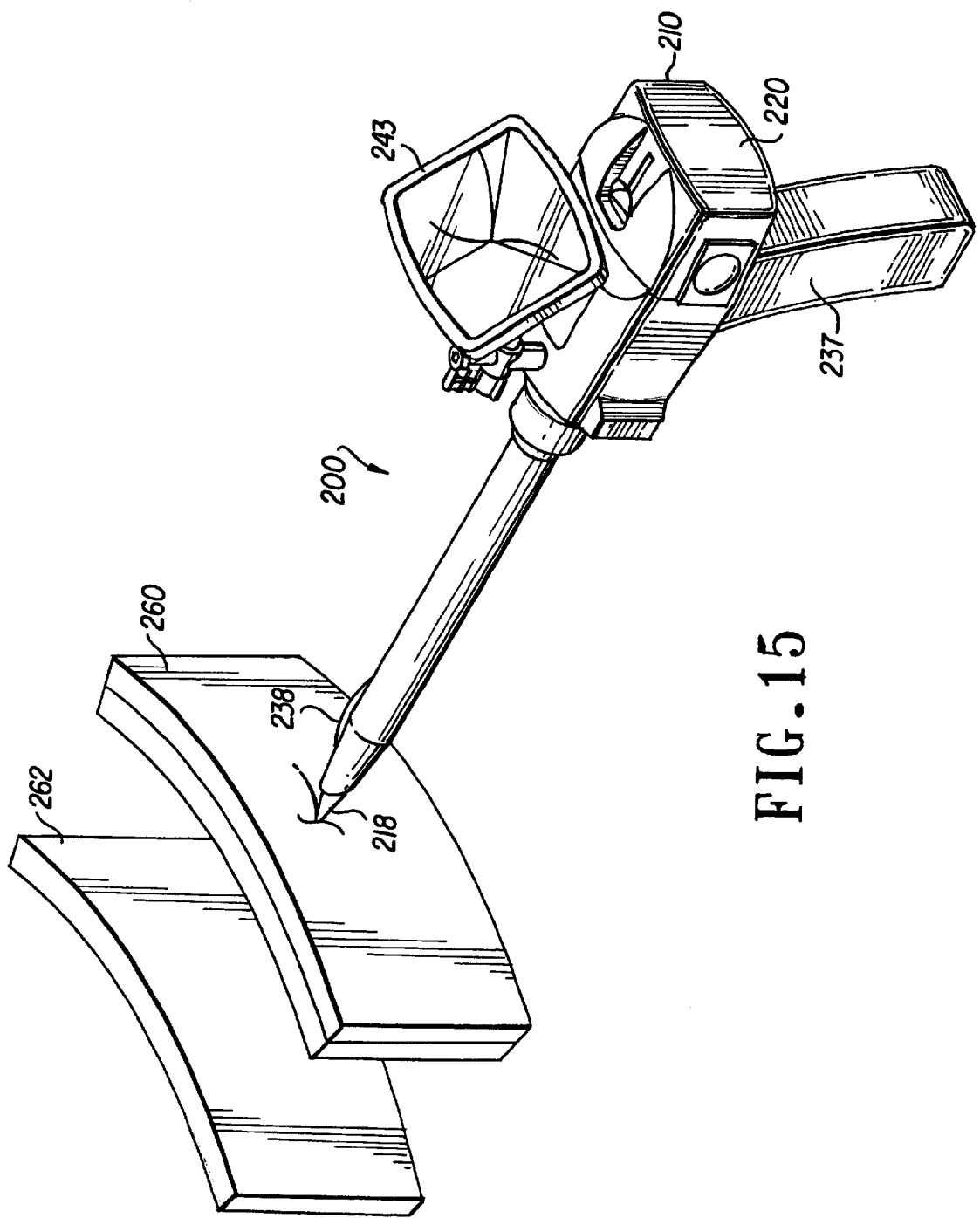
FIG. 15 is a perspective illustration of the penetrating endoscope of FIGS. 7 and 8 in use, before penetrating an outer tissue wall.
Figure 16:
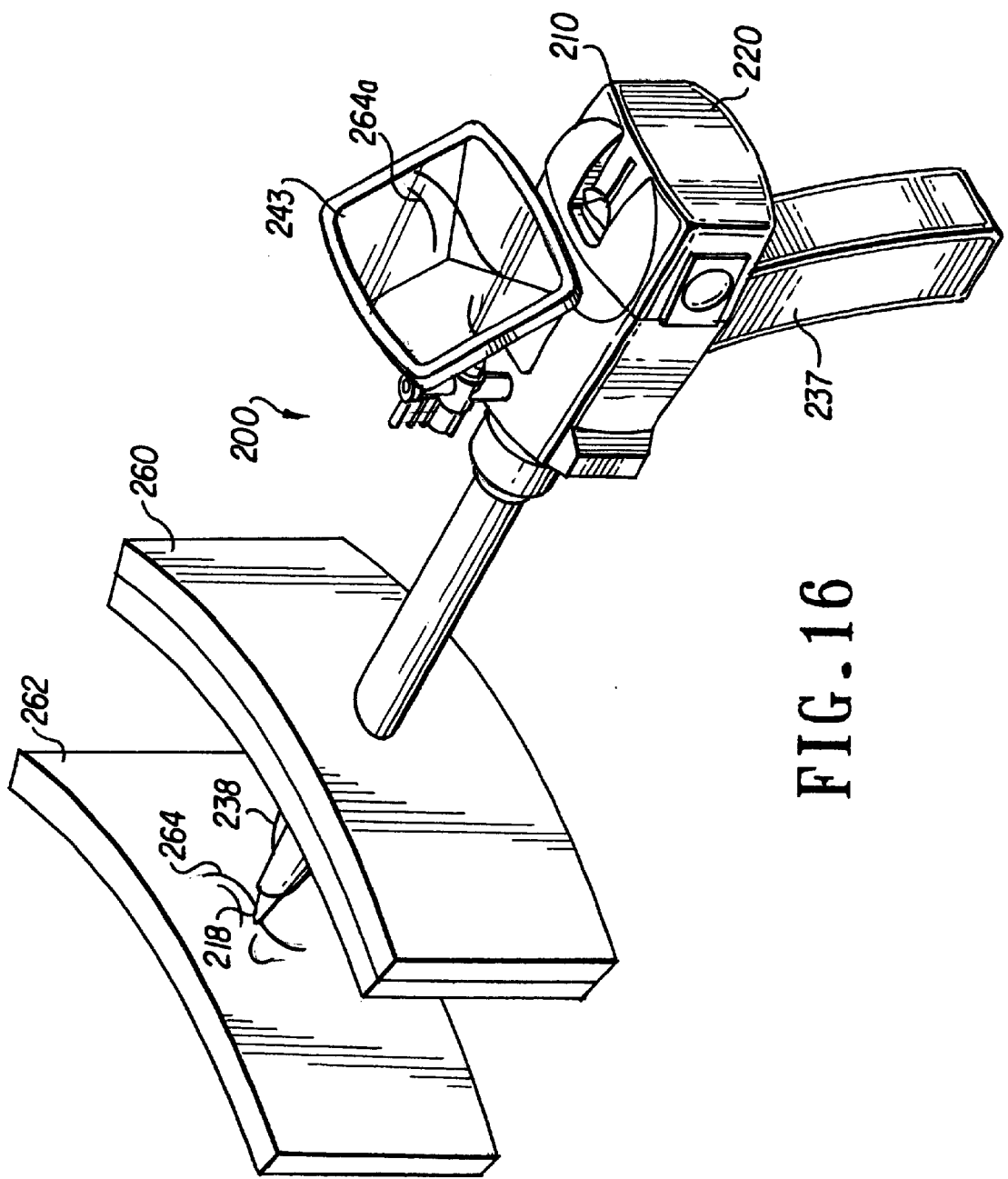
FIG. 16 is a perspective illustration of the penetrating endoscope of FIG. 15 in use, after penetrating an outer tissue wall.

Turning now to FIGS. 15, 16 and 17, the third embodiment of the penetrating endoscope 200 (FIGS. 7 and 8) is illustrated. As shown in FIG. 15, penetrating endoscope 200 is positioned against the outer tissue wall 260 in preparation for penetrating through the tissue wall using sharp distal end 218 containing penetrating member CMOS image sensor 220, the view from which is shown on display 243. The surgeon grasps handle 237 and applies sufficient force to the penetrating endoscope 200 to force the sharp distal end through outer tissue wall 260 while viewing the field of view of the penetrating member image sensor 222 on display 243. Once the surgeon has forced sharp distal end 218 through outer tissue wall 260, the interior of the body and, more particularly, interior organ wall 262 are illuminated and become visible to both the penetrating member image sensor 22 and the portal sleeve image sensor 238.

In the method of the present invention, display 243 receives image signal information from the penetrating member image sensor 222 so long as penetrating member 210 is within portal sleeve 212. The surgeon grasps penetrating member housing 220 and removes penetrating member 210 from portal sleeve 212, thereby leaving only the portal sleeve image sensor 238 disposed within the body, as shown in FIG. 17. Once penetrating member 210 has been withdrawn, the image control module disposed within portal sleeve housing 236 switches the image signal provided to display 243 to show an image corresponding to the image signal generated by portal sleeve image sensor 238.

For purposes of illustration, FIG. 16 shows the organ wall surface features 264 from perspective of the penetrating member image sensor 222 on display 243 as image 264a. Once penetrating member 210 has been withdrawn, as shown in FIG. 17, the perspective shown on display 243 is shifted slightly and offset as display image 264b. The offset image 264b generated in the portal sleeve image sensor 238 is displaced laterally from the first image 264a generated by the penetrating member image sensor 222. In the embodiment and methods illustrated in FIGS. 15, 16 and 17, the surgeon continues to view the interior organ wall 262 during any subsequent surgical steps.

Figures 18, 24:
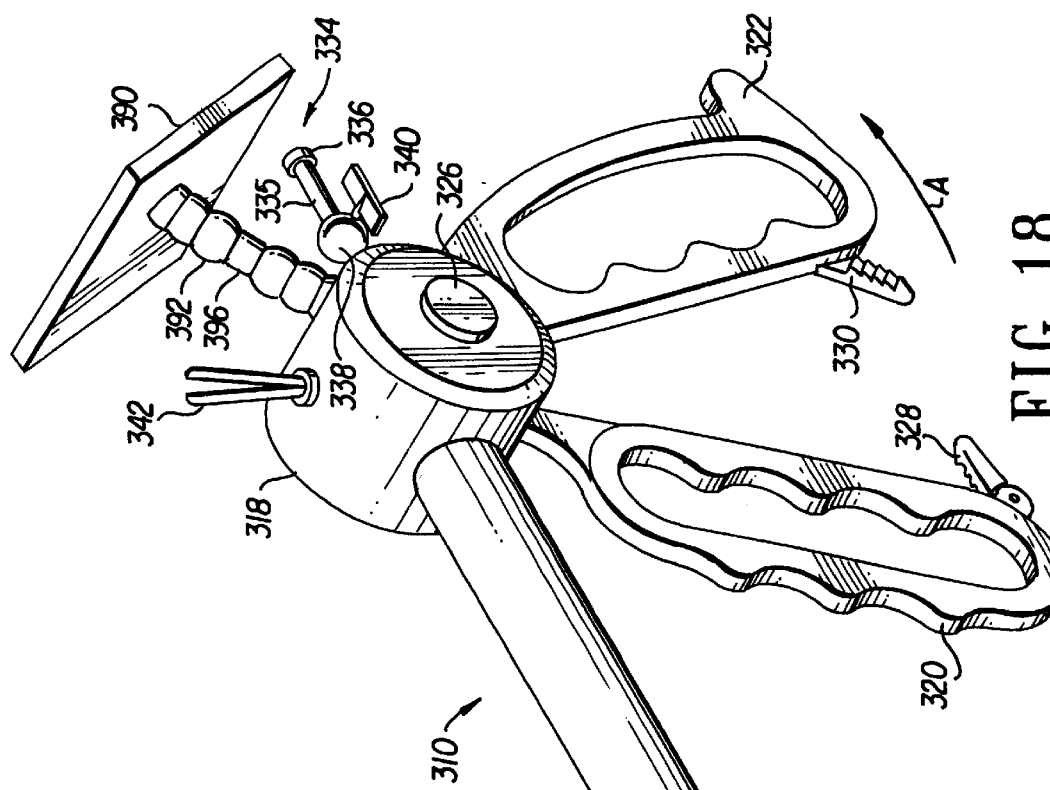
FIG. 18 is a perspective illustration of a surgical instrument including a solid-state endoscope.
FIG. 24 is a partial cross section of the endoscope distal end of FIGS. 21 and 23 showing a cross section of the sealed optics package taken in a plane parallel to the optical axis and perpendicular to the image plane.

In an alternative embodiment of the present invention, as illustrated in FIG. 18, an endoscopic surgical instrument 310 can be used to visualize anatomical tissue, organ structures or foreign objects in an anatomical cavity or elsewhere in the body. While the instrument 310 is described hereinafter for use with a tubular portal sleeve (not shown) in endoscopic procedures, such as laparoscopy, the instrument can be used in open surgery or with catheters or other small and large diameter tubular or hollow cylindrical members providing access to small cavities (e.g., veins or arteries) or large cavities (e.g., the abdomen); portal, for purposes of the present invention, is defined as any opening into the body, incised or natural.

The endoscopic instrument according to a first embodiment of the present invention is illustrated in FIGS. 18 and 19 and includes an elongate cylindrical barrel, or outer shaft 312 with a longitudinal axis and preferably having one or more elongated lumens or passages defined therein (preferably in the form of one or more channels, e.g., 314), a barrel distal end 315 for being disposed in the body and a barrel proximal end terminating in and carried by a housing 318 including an exterior wall enclosing an interior volume. Housing 318 includes scissor type handles 320 and 322 for controlling surgical instruments such as forceps having jaw members 324, 325 (as best seen in FIG. 19), or other end effectors. Housing 318 also includes a transversely located button 326 for selectively disengaging the scissor type handles 320 and 322 and permitting rotation of the handles about the axis of rotation (as indicated by the arrow A in FIG. 18). Handles 320, 322 are connected through a linkage mechanism (as is well known in the art) to at least one jaw; in the example of FIG. 18, movable jaw 324 is responsive to the separation between handles 320, 322, such that spreading handles 320, 322 apart opens jaw 324, separating jaw 324 from fixed jaw 325.

Handle rotation allows the surgeon to orient handles 320 and 322 in a desired manner, before or during surgery. The handles 320 and 322 also include serrated lock protrusions 328 and 330 to interlock and allow the position of handles 320 and 322 to be maintained in a state corresponding to a desired position of the end effectors (e.g., forceps jaws 324, 325). Lock protrusions 328 and 330 can be pivoted to a position to prevent interlock, if desired. Handles 320 and 322 are configured to be grasped while the surgeon's fingers pass through the openings in the handles or while the surgeon's fingers are wrapped around the outer portions of the handles, to increase comfort and adaptability.

The channel 314 in hollow barrel 312 is a lumen or passage adapted to receive elongate surgical instruments including a tubular body or member with a proximal end and a distal end being insertable at the proximal end of the barrel channel (e.g., at proximal end 334); channel 314 extends through proximal tubular body 335, which carries a Luer lock 336 and a spherical reservoir 338 for receiving a stop-cock valve 340, thereby allowing channel 314 to be selectably opened or sealed at the instrument proximal end. Housing 318 includes a cautery electrode connection 342 for removable electrical connection to a source of electrical energy for cauterizing tissue by passing electrical current through the end effectors (e.g., forceps jaws 324, 325 as illustrated in FIG. 19).

Turning now to FIGS. 19 and 20, a substantially planar CMOS image sensor 350 includes a plurality of pixels (e.g., in a rectangular grid, 640 pixels by 480 pixels) and is affixed to and carried by instrument barrel distal end 315. The CMOS image sensor is integrated onto a chip 350e, preferably incorporated into a sealed optics package 350a including one or more objective lens elements 350b and a printed circuit board or substrate 350c carrying electrical connections between electrical conductors or wires 350d and the CMOS image sensor chip 350e; the sealed optics package 350a is mounted onto or integrated in the distal end 315 of the endoscope shaft 312, preferably proximate a fiber optic end 352.

By CMOS image sensor is meant a solid-state image sensor fabricated using the well known, economical, complementary metal oxide semiconductor (CMOS) process, i.e., the Integrated Circuit (IC) fabrication technology usually combining either or both of enhancement mode N-channel (NMOS) and enhancement mode P-channel (PMOS) Field Effect Transistors (FETs), preferably on a single substrate to form logic gates, memory cells, or image sensor pixels. CMOS image sensors are fabricated using the CMOS process and preferably incorporate, on a single substrate (or chip), image signal processing, memory, and data transmission circuitry to generate image ready signals and transfer the image ready signals out of the body. By image ready signal is meant a signal processed and adapted to be readily displayed on an image display. Any of several standards for image signal processing and transmission are suitable; for example, signal processing circuits on chip 350e can convert periodically sampled individual pixel voltage (or current) levels into a National Television System Committee (NTSC) image signal for transmission out of the body and display on an NTSC compatible image display (e.g., television).

The CMOS image sensor 350 preferably has a plurality of MOS pixel circuits integrated onto chip 350e proximate a Red-Green-Blue (RGB) mosaic color filter panel 350f (as shown in FIG. 20) constituted by a mosaic arrangement of red, green, and blue color filters (or optionally, cyan, magenta and yellow color filters), thus permitting any single pixel to receive either red, green or blue (or cyan, magenta and yellow) filtered light energy. The color mosaic filter panel 350f is disposed on the optical axis of optics package 350a, ahead of the transverse imaging surface of the CMOS chip 350e. The pixels receiving red, green, and blue light generate, respectively, red, green, and blue pixel light intensity values, for color image ready signal generation. The lens elements 350b comprising the objective lens in sealed optics package 350a are preferably fixed in position providing a fixed depth of field at an image plane substantially coincident with a plane containing the pixels of CMOS image sensing chip 350e. The optical axis 350i (shown as a dotted line through sealed optics package 350a in FIG. 20) extends linearly from the image light transmissive, sealed protective cover or window 350h mounted on barrel distal end 315, proximally to image sensing chip 350e being disposed transverse thereto, in the image plane. The objective lens comprised of lens elements 350b focuses an image corresponding to the endoscope field of view at the image plane intersecting and transverse to the optical axis 350i. The objective lens is preferably fixed focus, meaning that a fixed depth of field is provided having a selected minimum in-focus distance 350g.

The objective lens elements 350b in sealed optics package 350a are selected and positioned to define a focal plane coincident with the image plane of image sensor chip 350e. Optionally, the objective lens elements 350b may be individually movable using a motorized focus control mechanism and may also provide variable magnification (i.e., zoom), as is known in the art. In the preferred embodiment, however, the lens elements are fixed in position to provide an in-focus image at all distances from the barrel distal end 315 greater than selected minimum in-focus distance 350g. Fixed focus optics are preferred for disposable embodiments. As shown in FIG. 20, the fixed focus optics of the sealed optics package 350a provide a minimum focus distance 350g (i.e., a minimum distance from the objective lens elements for which an observed object will remain in focus) less than or equal to the length of the forceps jaw 325 (or the length of any other surgical instrument end effector), thus ensuring that the surgeon can see a focused image of objects just within the grasp of the end effector, and beyond.

Ask shown in FIG. 18, surgical instrument 310 preferably includes a distally mounted adjustable image display 390 carried on housing 318. Display 390 can be a Liquid Crystal Display (LCD), a flat panel plasma display or a High Intensity Discharge (HID) display, mounted on a flexible stalk 392 for convenient repositioning during a surgical procedure. The display is preferably release-ably connectable using a locking electrical connector 396, thereby permitting removal of display 390 before sterilizing or discarding endoscopic instrument 310, after use.

A proximal light source is carried within the interior volume of housing 318 and is selectively energized to provide illumination transmitted distally through a fiber optic waveguide within barrel 312 and radiated distally from fiber optic distal end 352. Light radiating distally from fiber optic end 352 illuminates substantially all of the field of view of CMOS image sensor 350 and can be turned on or off by operation of a micro-switch (not shown) carried on housing 318. The light source is powered electrically through a housing cable proximally terminated in an electrical connector, or via a battery preferably carried within housing 318.

In an alternative embodiment of the present invention illustrated in FIGS. 21, 22, 23, 24 and 25, a surgical instrument 356 has a housing carrying an elongate hollow barrel including a lumen or channel 358 with an elongate endoscope 360 extending through at least a portion of barrel channel 358. Elongate tubular endoscope 360 includes a cylindrical member, body or barrel 362 having a distal end 64 adapted to be slidably received within instrument channel 358 and opposite a proximal endoscope housing 366 carried upon endoscope proximal end 368. A light source is contained within housing 366 and provides light transmitted distally through a fiber optic bundle 370 terminating distally in fiber optic end 372.

Figure 23:
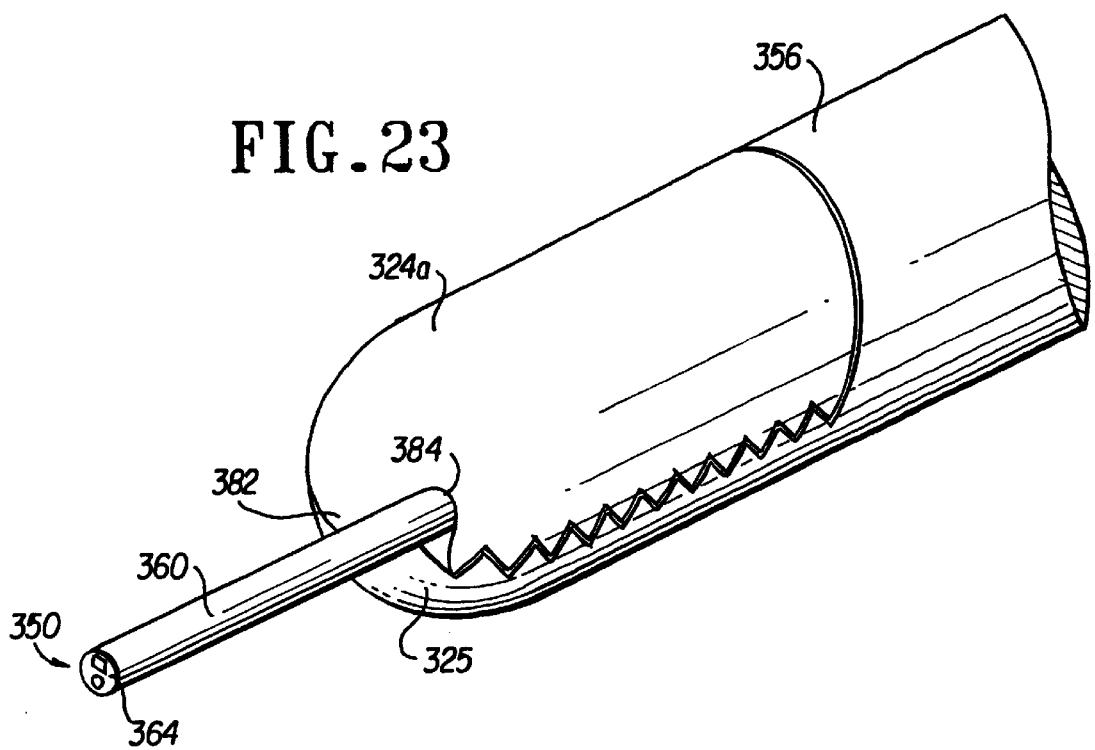
FIG. 23 is an enlarged perspective illustration of the distal end of the surgical instrument of FIG. 21.

As shown in FIGS. 23 and 24, a CMOS image sensor 350 is affixed to and carried by distal end 364 of the elongate member or body 362 of tubular endoscope 360 and provides a distally aimed endoscope field of view. Light radiating distally from fiber optic end 372 illuminates substantially all of the field of view of CMOS image sensor 350 and is turned on or off by operation of a micro-switch (not shown) carried on housing 366. The light source is powered electrically through a housing cable 376 proximally terminated in an electrical connector 378 (as shown in FIG. 22).

CMOS image sensor 350 preferably includes a rectangular array (e.g., 640×480) of MOS pixel circuits integrated onto chip 350e proximate a Red-Green-Blue (RGB) mosaic color filter panel 350f (as shown in FIG. 24) constituted by a mosaic arrangement of red, green, and blue color filters (or, as above, cyan, magenta and yellow color filters), thus permitting any single pixel to receive either red, green or blue (or cyan, magenta and yellow) filtered light energy. The color mosaic filter panel 350f is disposed on the optical axis of optics package 350a, ahead of the transverse imaging surface of the CMOS chip 350e. The pixels receiving red, green, and blue light generate, respectively, red, green, and blue pixel light intensity values, for color image signal generation. The lens elements 350b comprising the objective lens in sealed optics package 350a are preferably fixed in position providing a fixed depth of field at an image plane substantially coincident with a plane containing the pixels of CMOS image sensing chip 350e. The optical axis 350i (shown as a dotted line through sealed optics package 350a in FIG. 24) extends linearly from the image light transmissive, sealed protective cover or window 350h mounted on member distal end 364, proximally to image sensing chip 350e being disposed transverse thereto, in the image plane. The objective lens comprised of lens elements 350b focus an image corresponding to the endoscope field of view at the image plane intersecting and transverse to the optical axis 350i. The objective lens is fixed focus, meaning that a fixed depth of field is provided having a selected minimum in-focus distance (e.g., one centimeter).

Figure 25:
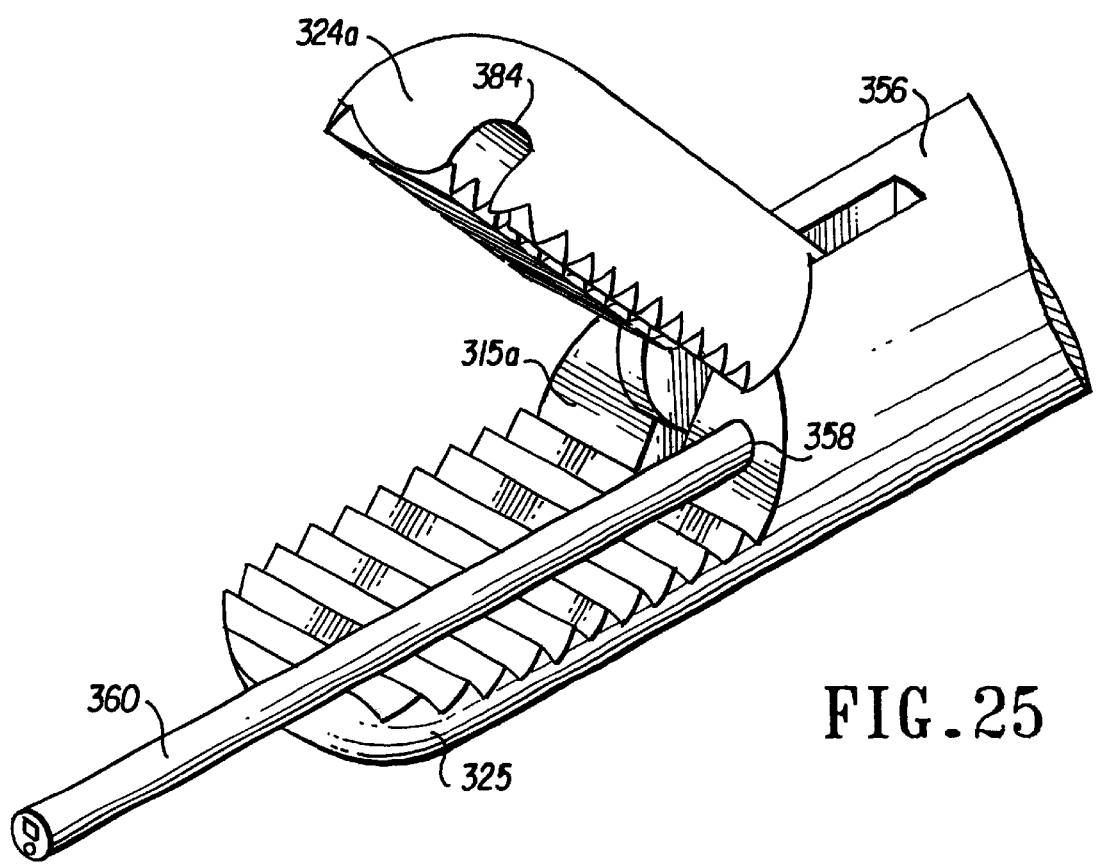
FIG. 25 is an enlarged perspective illustration of the distal end of the surgical instrument of FIG. 21, with the jaws shown in the open position.

The objective lens elements 350b in sealed optics package 350a are selected and positioned to provide a focal plane coincident with the image plane of image sensor chip 350e. Optionally, the objective lens elements 350b may be individually movable using a motorized focus control mechanism and may also provide variable magnification (i.e., zoom), as is known in the art. In the preferred embodiment, however, the lens elements are fixed in position to provide an in-focus image at all distances from the endoscope distal end 364 greater than the selected minimum in-focus distance. As shown in FIG. 24, the fixed focus optics of the sealed optics package 350a provide a minimum focus distance (i.e., a minimum distance from the objective lens window 350h or member distal end 364 for which an observed object will remain in focus) less or equal to the length of fixed forceps jaw 325 (or the length of any other surgical instrument end effector), thus ensuring that the surgeon can see a focused image of objects just within the grasp of the end effector, and beyond, when the endoscope 360 is slidably positioned within channel 358 with endoscope distal end 364 aligned with (i.e., even with and not projecting beyond) barrel distal end 315a. Alternatively, endoscope 360 may be translated distally to project well beyond the barrel distal end 315a (as shown in FIG. 25) in which case objects beyond the minimum in-focus distance (and further) will be in focus at the image plane coincident with CMOS image sensor chip 350e.

The semiconductor chip 350e includes a CMOS imaging sensor and, preferably, a microprocessor and a signal processing circuit for generating image ready signals for transmission to a display and to a data logging computer, outside the body. Image signal data is transmitted proximally from CMOS image sensor 350, preferably via an image signal cable 380 running just within the exterior surface of barrel 362. Preferably, image ready data is transmitted proximally and out of the body to a movably adjustable, release-ably connect-able display 390 and/or to an image data logging recorder or computer (not shown) through an image data cable electrically connected with image signal cable 380.

As noted above, in the embodiment of FIGS. 21, 22, 23, 24 and 25, endoscope 360 may be advanced distally through channel 314, up to and beyond the distal end 382 of forceps jaws 324a, 325. Preferably at least one jaw 324a (or other end effector) includes a groove 384 to permit endoscope 360 (or another surgical instrument) to pass therethrough when the jaws are closed (as shown in FIG. 23).

As shown in FIGS. 21 and 22, surgical instrument 356 preferably includes proximally mounted adjustable image display 390 carried on a flexible stalk 392 for convenient repositioning during a surgical procedure and preferably release-ably connect-able using a locking electrical connector 396, thereby permitting removal of display 390 before sterilizing or discarding endoscopic instrument 356 after use.

The endoscopic instruments of the present invention (e.g., 360) may be aimed to provide the desired field of view of a procedure and may include a sealed optics package in the form of an articulable ball joint having the CMOS imaging sensor and a light source for illuminating the field of visualization; the ball joint imaging sensor aim is preferably articulable or controllable from the instrument proximal end using wire control members connected to housing mounted control wheels.

In an alternative embodiment, the endoscope has a fixed objective lens carried on the distal end of a tubular body and a lens train or fiberoptic bundle transmits the endoscopic image proximally to a CMOS image sensor located in a housing (e.g., 318 or 366).

Figure 26:
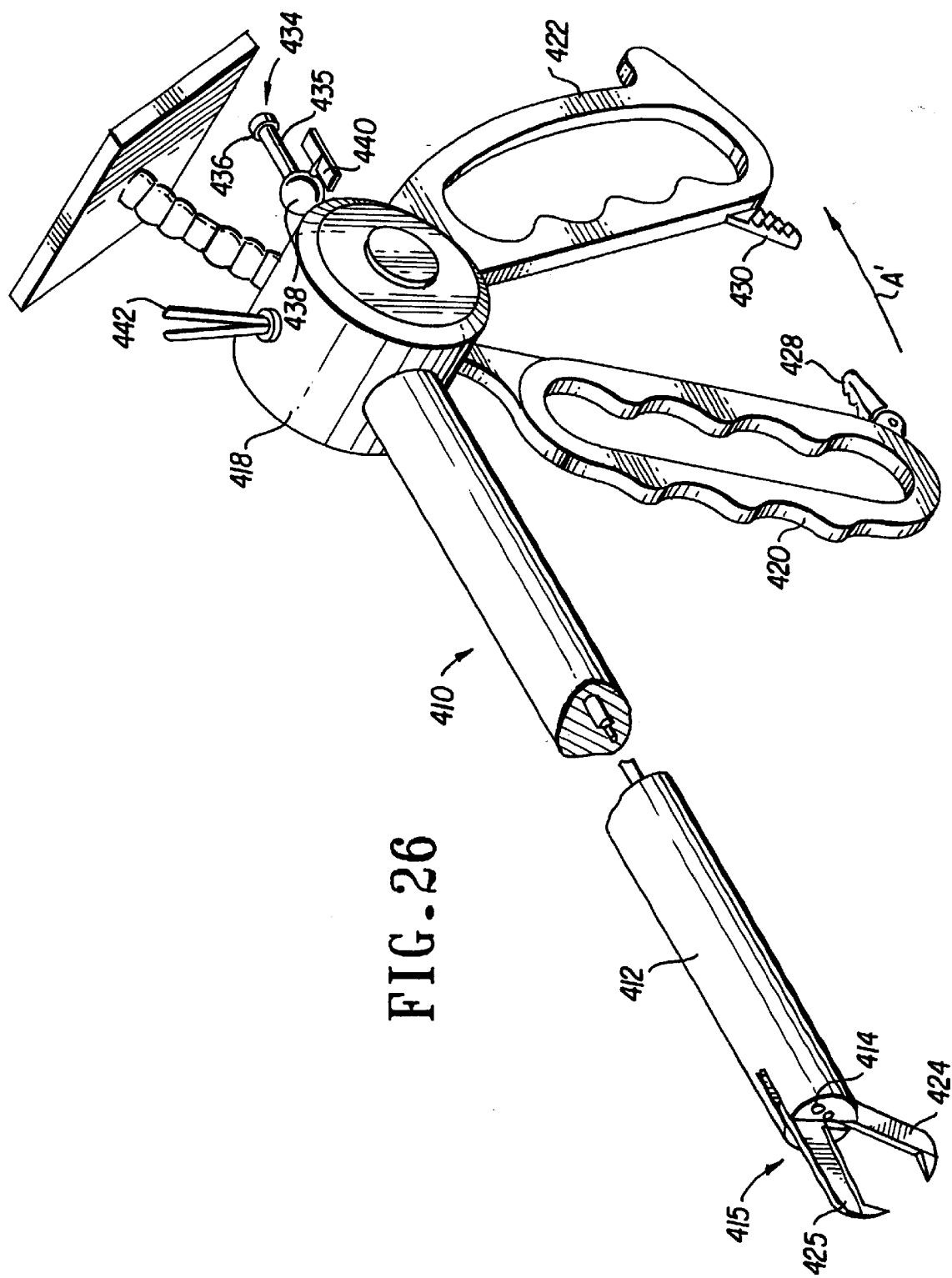
FIG. 26 is a perspective illustration of a surgical instrument including a solid-state endoscope.

In accordance with another alternative embodiment of the present invention, as illustrated in FIG. 26, an endoscopic surgical instrument 410 can be used to visualize anatomical tissue, organ structures or foreign objects in an anatomical cavity or elsewhere in the body. While the instrument 410 is described hereinafter for use with a tubular portal sleeve (not shown) in endoscopic procedures, such as laparoscopy, the instrument can be used in open surgery or with catheters or other small and large diameter tubular or hollow cylindrical members providing access to small cavities (e.g., veins or arteries) or large cavities (e.g., the abdomen); portal, for purposes of the present invention, is defined as any opening into the body, incised or natural.

The endoscopic instrument according to another alternative embodiment of the present invention is illustrated in FIGS. 26, 27, 28 and 29 and includes an elongate cylindrical barrel, or other shaft 412 with a longitudinal axis and preferably having one or more elongated lumens or passages defined therein (preferably in the form of one or more channels, e.g., 414), a barrel distal end 415 for being disposed in the body and a barrel proximal end terminating in and carried by a housing 418 including an exterior wall enclosing an interior volume. Housing 418 includes scissor type handles 420 and 422 for controlling surgical instruments such as a cutting end effector having cutting jaw members 424, 425 (as best seen in FIG. 27), or other end effectors. Housing 418 also includes a transversely located button 426 for selectively disengaging the scissor type handles 420 and 422 and permitting rotation of the handles about the axis of rotation (as indicated by the arrow A' in FIG. 26). Handles 420, 422 are connected through a linkage mechanism (as is well known in the art) to at least one jaw; in the example of FIG. 26, movable jaw 424 is responsive to the separation between handles 420, 422, such that spreading handles 420, 422 apart opens jaw 424, separating jaw 424 from fixed jaw 425.

Figure 32:
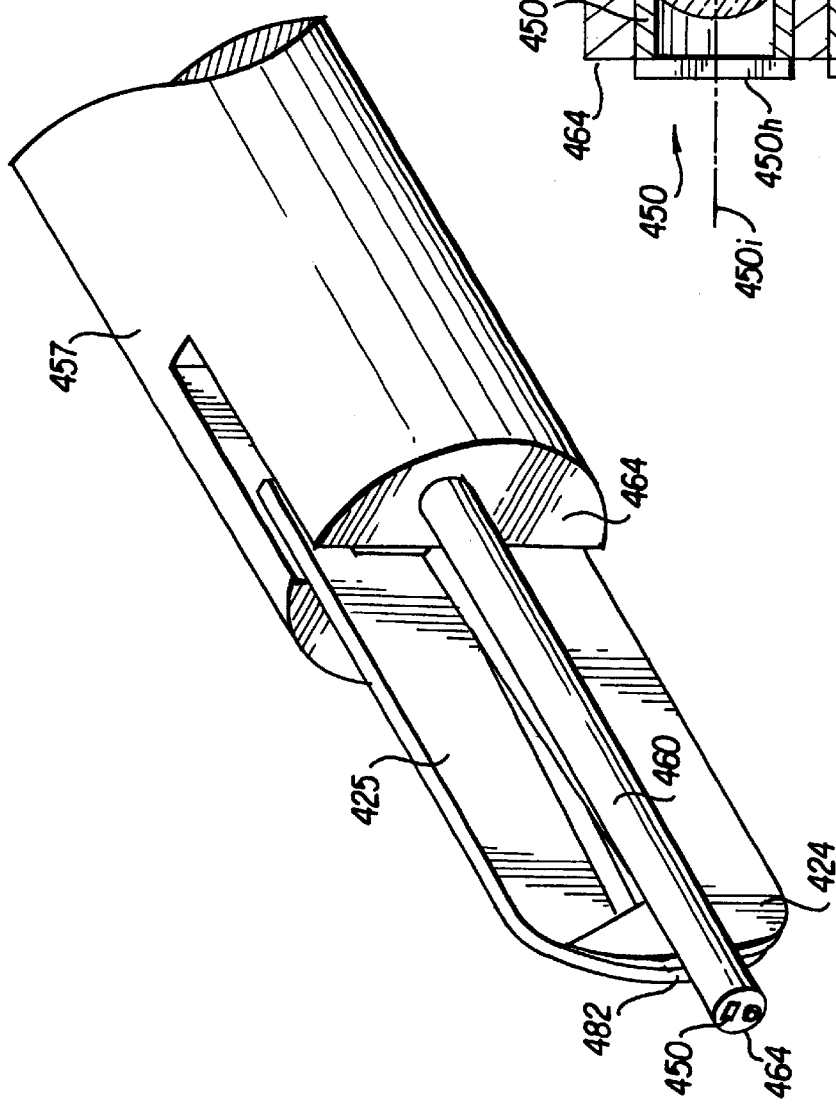
FIG. 32 is an enlarged perspective illustration of the distal end of the surgical instrument of FIG. 30.

As best seen in FIGS. 27 and 28, jaws 424 and 425 are hingedly carried by barrel 412 adjacent the barrel distal end 415. The jaws are shown in a fully open position in FIGS. 27 and 28 and are closed in a continuous movement to assume the closed position illustrated in FIGS. 30 and 32. Upper cutting jaw 425 includes a substantially planar blade member substantially aligned with the central axis of barrel 412 and includes a cutting edge 425a having a selected edge length and terminated distally in a tapered transverse barb 425b; similarly, lower, movable cutting jaw 424 includes a substantially planar blade member substantially aligned with the central axis of barrel 412 and includes a cutting edge 424a having a selected edge length and terminated distally in a tapered transverse barb 424b. When the cutting jaws 424, 425 are in the closed position, transverse barbs 424b, 425b overlap, as shown in FIG. 32.

Handle rotation allows the surgeon to orient handles 420 and 422 in a desired manner, before or during surgery. The handles 420 and 422 also include serrated lock protrusions 428 and 430 to interlock and allow the position of handles 420 and 422 to be maintained in a state corresponding to a desired position of the end effector jaws 424, 425. Lock protrusions 428 and 430 can be pivoted to a position to prevent interlock, if desired. Handles 420 and 422 are configured to be grasped while the surgeon's fingers pass through the openings in the handles or while the surgeon's fingers are wrapped around the outer portions of the handles, to increase comfort and adaptability.

The channel 414 in hollow barrel 412 is a lumen or passage adapted to receive elongate surgical instruments including a tubular body or member with a proximal end and a distal end being insertable at the proximal end of the barrel channel (e.g., at proximal end 434); channel 414 extends through proximal tubular body 435, which carries a Luer lock 436 and a spherical reservoir 438 for receiving a stop-cock valve 440, thereby allowing channel 414 to be selectably opened or sealed at the instrument proximal end. Housing 418 includes a cautery electrode connection 442 for removable electrical connection to a source of electrical energy for cauterizing tissue by passing electrical current through the end effector jaws 424, 425, as illustrated in FIG. 26.

Figure 29:
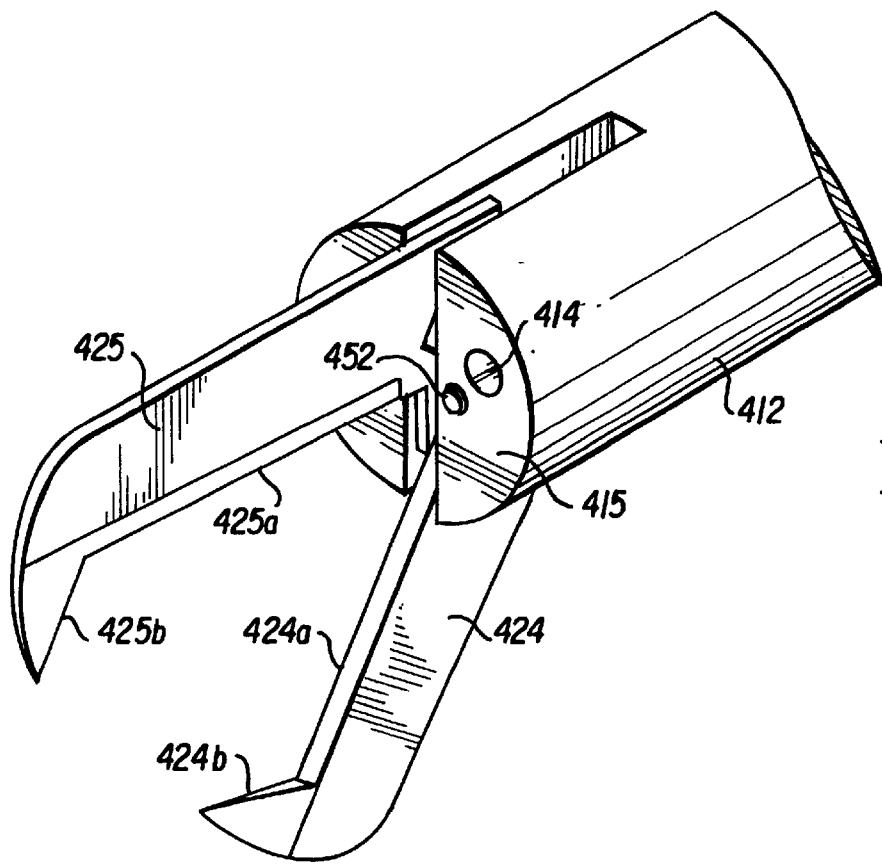
FIG. 29 is an enlarged perspective illustration of the distal end right side of the surgical instrument of FIG. 26.
Figure 34:
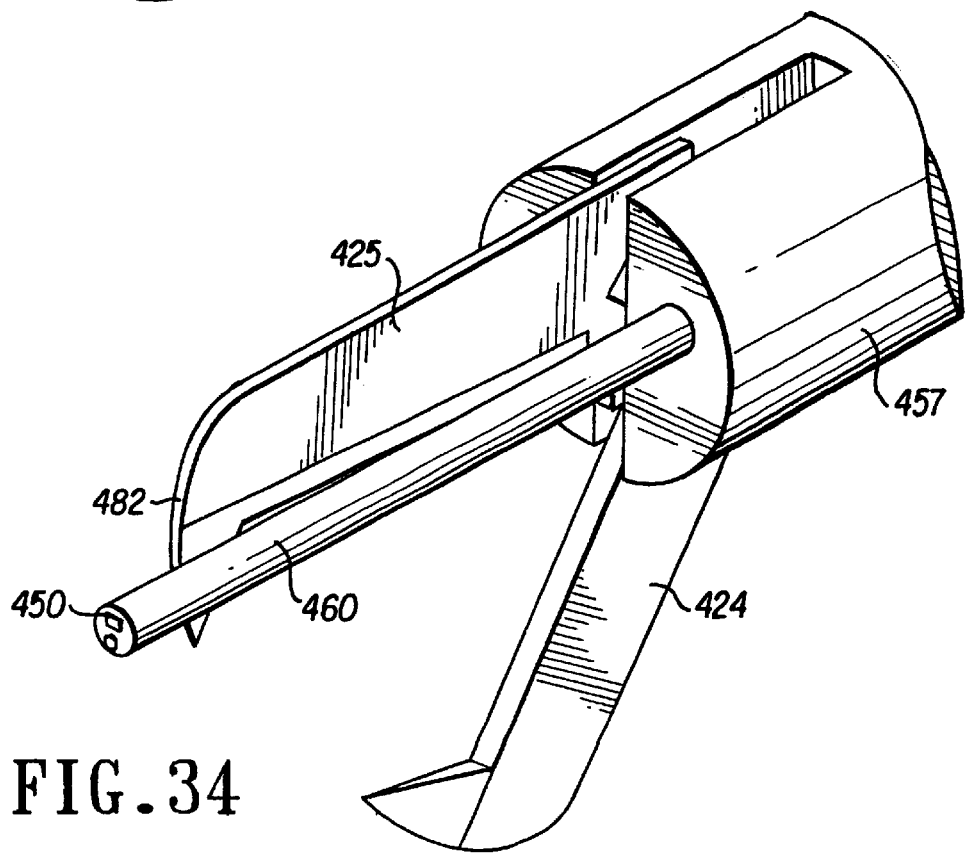
FIG. 34 is an enlarged perspective illustration of the distal end of the surgical instrument of FIGS. 30 and 33, with the cutting end effector jaws shown in the open position.

Turning now to FIGS. 27 and 28, a substantially planar CMOS image sensor 450 includes a plurality of pixels (e.g., in a rectangular grid, 640 pixels by 480 pixels) and is affixed to and carried by instrument barrel distal end 415. The CMOS image sensor is integrated onto a chip 450e, preferably incorporated into a sealed optics package 450a including one or more objective lens elements 450b and a printed circuit board or substrate 450c carrying electrical connections from connecting wires 450d to the CMOS image sensor chip 450e; the sealed optics package 450a is mounted onto or integrated in the distal end 415 of the endoscope shaft 412, preferably proximate a fiber optic end 452 (as best seen in FIG. 29).

Any of several standards for image signal processing and transmission regarding the CMOS sensor are suitable; for example, signal processing circuits on chip 450e can convert periodically sampled individual pixel voltage (or current) levels into a National Television System Committee (NTSC) image signal for transmission out of the body and display on an NTSC compatible image display (e.g., a television).

The CMOS image sensor 450 preferably has a plurality of MOS pixel circuits integrated onto chip 450e proximate a Red-Green-Blue (RGB) mosaic color filter panel 450f (as shown in FIG. 28) constituted by a mosaic arrangement of red, green, and blue color filters (or optionally, cyan, magenta and yellow color filters), thus permitting any single pixel to receive either red, green or blue (or cyan, magenta and yellow) filtered light energy. The color mosaic filter panel 450f is disposed on the optical axis of optics package 450a, ahead of the transverse imaging surface of the CMOS chip 450e. The pixels receiving red, green, and blue light generate, respectively, red, green, and blue pixel light intensity values, for color image ready signal generation. The lens elements 450b comprising the objective. lens in sealed optics package 450a are preferably fixed in position providing a fixed depth of field at an image plane substantially coincident with a plane containing the pixels of CMOS image sensing chip 450e. The optical axis 450i (shown as a dotted line through sealed optics package 450a in FIG. 28) extends linearly from the image light transmissive, sealed protective cover or window 450h mounted on barrel distal end 415, proximal (or adjacent) to image sensing chip 450e which is disposed transverse to the optical axis and in the image plane. The objective lens comprised of lens elements 450b focuses an image corresponding to the endoscope field of view at the image plane intersecting and transverse to the optical axis 450i. The objective lens is preferably fixed focus, meaning that a fixed depth of field is provided having a selected minimum in-focus distance 450g.

The objective lens elements 450b in sealed optics package 450a are selected and positioned to define a focal plane coincident with the image plane of image sensor chip 450e. Optionally, the objective lens elements 450b may be individually movable using a motorized focus control mechanism and may also provide variable magnification (i.e., zoom), as is known in the art. In the preferred embodiment, however, the lens elements are fixed in position to provide an in-focus image at all distances from the barrel distal 415 greater than selected minimum in-focus distance 450g. Fixed focus optics are preferred for disposable embodiments. As shown in FIG. 28, the fixed focus optics of the sealed optics package 450a provide a minimum focus distance 450g (i.e., a minimum distance from the objective lens elements for which an observed object will remain in focus) less than or equal to the length of the edge 425a of cutting jaw 425 (or the length of any other surgical instrument and effector), thus ensuring that the surgeon can see a focused image of objects just within the grasp of the end effector (e.g., within the grasp of the transverse barbs 424b, 425b), and beyond.

As shown in FIG. 26, surgical instrument 410 preferably includes a distally mounted adjustable image display 490 carried on housing 418. Display 490 can be a Liquid Crystal Display (LCD), a flat panel plasma display, a High Intensity Discharge (HID) display or a solid state display (e.g., including a CMOS display panel), mounted on a flexible stalk 492 for convenient repositioning during a surgical procedure. The display is preferably release-ably connectable using a locking electrical connector 496, thereby permitting removal of display 490 before sterilizing or discarding endoscopic instrument 410, after use.

A proximal light source is carried within the interior volume of housing 418 and is selectively energized to provide illumination transmitted distally through a fiber optic waveguide within barrel 412 and radiated distally from fiber optic distal end 452. Light radiating distally from fiber optic end 452 illuminates substantially all of the field of view of CMOS image sensor 450 and can be turned on or off by operation of a micro-switch (not shown) carried on housing 418. The light source is powered electrically through a housing cable proximally terminated in an electrical connector, or via a battery preferably carried within housing 418.

In an alternative embodiment of the present invention illustrated in FIGS. 30, 31, 32, 33 and 34, a surgical instrument 456 has a housing carrying an elongate hollow barrel 457 including a lumen or channel 458 with an elongate tubular endoscope 460 extending through at least a portion of barrel channel 458. Elongate tubular endoscope 460 includes a cylindrical member or body 462 having distal end 464 (adapted ro be slidably received within instrument channel 458) opposing a proximal endoscope housing 466 carried upon endoscope proximal end 468. A light source is contained within housing 466 and provides light transmitted distally through a fiber optic bundle 470 terminating distally in fiber optic end 472.

Figure 33:
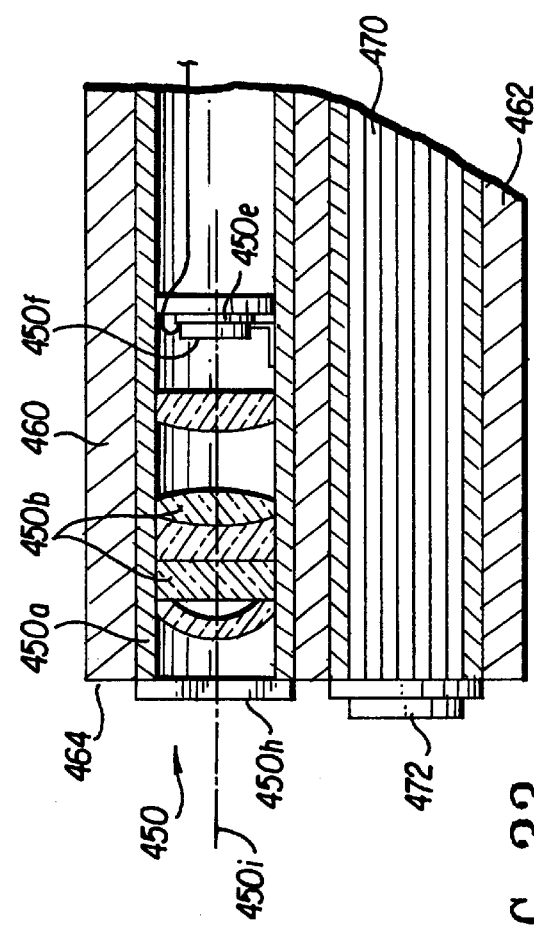
FIG. 33 is a partial cross section of the endoscope distal end of FIGS. 30 and 32 showing a cross section of the sealed optics package taken in a plane parallel to the optical axis and perpendicular to the image plane.

As best seen in FIGS. 32 and 33, a CMOS image sensor 450 is affixed to and carried by distal end 464 of the elongate member or body 462 of tubular endoscope 460 and provides a distally aimed endoscope field of view. Light radiating distally from fiber optic end 472 illuminates substantially all of the field of view of CMOS image sensor 450 and is turned on or off by operation of a micro-switch (not shown) carried on housing 466. The light source is powered electrically through a housing cable 476 proximally terminated in an electrical connector 478 (as shown in FIG. 30).

CMOS image sensor 450 preferably includes a rectangular array (e.g., 640×480) of MOS pixel circuits integrated onto chip 450e proximate a Red-Green-Blue (RGB) mosaic color filter panel 450f (as shown in FIG. 32) constituted by a mosaic arrangement of red, green, and blue color filters (or, as above, cyan, magenta and yellow color filters), thus permitting any single pixel to receive either red, green or blue (or cyan, magenta and yellow) filtered light energy. The color mosaic filter panel 450f is disposed on the optical axis of optics package 450a, ahead of the transverse imaging surface of the CMOS chip 450e. The pixels receiving red, green, and blue light generate, respectively, red, green, and blue pixel light intensity values, for color image signal generation. The lens elements 450b comprising the objective lens in sealed optics package 450a are preferably fixed in position providing a fixed depth of field at an image plane substantially coincident with a plane containing the pixels of CMOS image sensing chip 450e. The optical axis 450i (shown as a dotted line through sealed optics package 450a in FIG. 33) extends linearly from the image light transmissive, sealed protective cover or window 450h mounted on member distal end 464, adjacent to image sensing chip 450e being disposed transverse thereto, in the image plane. The objective lens comprised of lens elements 450b focus an image corresponding to the endoscope field of view at the image plane intersecting and transverse to the optical axis 450i. The objective lens is fixed focus, meaning that a fixed depth of field is provided having a selected minimum in-focus distance (e.g., one centimeter).

The objective lens elements 450b in sealed optics package 450a are selected and positioned to provide a focal plane coincident with the image plane of image sensor chip 450e. Optionally, the objective lens elements 450b may be individually movable using a motorized focus control mechanism and may also provide variable magnification (i.e., zoom), as is known in the art. In the preferred embodiment, however, the lens elements are fixed in position to provide an in-focus image at all distances from the body distal end 464 greater than the selected minimum in-focus distance. As shown in FIG. 32, the fixed focus optics of the sealed optics package 450a provide a minimum focus distance (i.e., a minimum distance from the objective lens window 450h mounted on or adjacent to member distal end 464 for which an observed object will remain in focus) less than or equal to the length of fixed cutting jaw 425 (or the length of any other surgical instrument end effector), thus ensuring that the surgeon can see a focused image of objects just within the grasp of the end effector, and beyond, when the endoscope 460 is slidably positioned within channel 458 with endoscope distal end 464 aligned with (i.e., even with and not projecting beyond) barrel distal end 415a. Alternatively, endoscope 460 may be translated distally to project well beyond the barrel distal end 415a (as shown in FIGS. 7 and 9) in which case objects beyond the minimum in-focus distance (and further) will be in focus at the image plane coincident with CMOS image sensor chip 450e.

Semiconductor chip 450e includes a CMOS imaging sensor and, preferably, a microprocessor and a signal processing circuit for generating image ready signals for transmission to a display and to a data logging computer, outside the body. Image signal data is transmitted proximally from CMOS image sensor 450, preferably via an image signal cable 480 running just within the exterior surface of barrel 462. Preferably, image ready data is transmitted proximally and out of the body to a movably adjustable, release-ably connect-able display 490 and/or to an image data logging recorder or computer (not shown) through an image data cable electrically connected with image signal cable 480.

As noted above, in the embodiment of FIGS. 30, 31, 32, 33 and 34, endoscope 460 may be advanced distally through channel 458, up to and beyond the distal end 482 of cutting jaws 424, 425, which are laterally offset therefrom.

As shown in FIGS. 30 and 31, surgical instrument 456 preferably includes proximally mounted adjustable image display 490 carried on a flexible stalk 492 for convenient repositioning during a surgical procedure and preferably release-ably connect-able using a locking electrical connector 496, thereby permitting removal of display 490 before sterilizing or discarding endoscopic instrument 456 after use.

The endoscopic instruments of the present invention (e.g., 460) may be aimed to provide the desired field of view of a procedure and may include a sealed optics package in the form of an articulable ball joint having the CMOS imaging sensor and a light source for illuminating the field of visualization; the ball joint imaging sensor aim is preferably articulable or controllable from the instrument proximal end using wire control members connected to housing mounted control wheels.

In an alternative embodiment, the endoscope has a fixed objective lens carried on the distal end of a tubular body and a lens train or fiberoptic bundle transmits the endoscopic image proximally to a CMOS image sensor located in a housing (e.g., 418 or 466).

It will be appreciated that the endoscope of the present invention, in each of the embodiments described herein, provides visualization of organ structures, tissue structures, prostheses and other foreign objects within the body, and all are adapted to be inserted through any portal into the body. Portal, as used herein, means any incised or natural opening providing access into the body. CMOS image sensor, as used herein includes all solid state integrated circuits fabricated by the well known CMOS process producing chips having a plurality of pixels for converting image light energy into electrical image signal energy. Preferably, the CMOS image sensor of the present invention includes, on the same chip or integrated circuit, an image processing circuit for converting periodically sampled pixel voltage (or current) levels into an image ready signal adapted for transmission out of the body (e.g., by electric signal conduction through wires or by transmission through an RF, microwave, ultrasonic, acoustic or fiber-optic data channel). An image ready signal, as used herein, means a signal processed and formatted (or otherwise adapted) for display on an image display or monitor. A CMOS image sensor pixel, as used herein, means a CMOS image sensor picture element, usually occupying a defined region in a two dimensional array, for gathering light in the defined region. For color images, a red pixel, a green pixel, and a blue pixel occupy three sub-regions within a color pixel region and red, green and blue color optical filters are incorporated into a color mosaic filter element and disposed adjacent to the respective CMOS image sensor pixel sub-regions. Depth of field, as used herein, describes the range of distances from the image sensor for which an object within the field of view will be in focus and resolved in sharp detail.

Inasmuch as the present invention is subject to various modifications and changes in detail, the above description of a preferred embodiment is intended to be exemplary only and not limiting. It is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A penetrating endoscope for providing visualization of organ or tissue structures or foreign objects in the body, comprising:

an elongate penetrating member having a longitudinal axis, a proximal end for being disposed externally and a sharp penetrating distal end adapted to be inserted into the body by penetrating anatomical tissue;

a substantially planar complementary metal oxide semiconductor (CMOS) image sensor including a plurality of pixels and a pixel signal processing circuit generating a color image ready signal, converting image light energy into electrical color image ready signal energy for transmission out of the body, said color image ready signal adapted to be viewed on a color image display;

said CMOS image sensor being carried on said elongate penetrating member adjacent said elongate penetrating member distal end;

an objective lens carried on said elongate penetrating member distal end on an optical axis and focusing an image corresponding to an endoscope field of view at an image plane intersecting said optical axis, said CMOS image sensor being mounted with said CMOS image sensor pixels disposed substantially in said image plane and on said optical axis; and said elongate penetrating member having an electrical contact on its proximal end in sliding engagement with another electrical contact for transmitting said image signal from the CMOS sensor to the image display.

2. The penetrating endoscope of claim 1, further including a source of illumination carried by said elongate member and illuminating said endoscope field of view.

3. The penetrating endoscope of claim 1, further including at least one fixed focus objective lens element having a depth of field with a selected minimum in-focus distance for an in-focus image at the image plane.

4. The penetrating endoscope of claim 3, said penetrating member having a tip of a selected axial length beyond said image plane, said axial length being substantially equal to or greater than said minimum in-focus distance, wherein said penetrating member tip is in focus at said image plane.

5. The penetrating endoscope of claim 3, further including a color mosaic optical filter disposed between said CMOS image sensor and said objective lens, said color mosaic optical filter being disposed on said optical axis.

6. A penetrating endoscope for viewing anatomical tissue or organ structures or other objects in the body, comprising:

a) an elongate hollow portal sleeve having a longitudinal axis, a proximal end for being disposed externally, a distal end for being disposed in the body and an open lumen extending from said proximal end through said distal end, said elongate hollow portal sleeve being adapted to be inserted into the body;

b) an endoscope comprising b1) an elongate penetrating member having a longitudinal axis, a proximal end and an optically clear penetrating distal end, said elongate member extending through at least a portion of said hollow portal sleeve lumen, b2) a substantially planar first complementary metal oxide semiconductor (CMOS) image sensor including a plurality of pixels and a pixel signal processing circuit generating an image ready signal, converting image light energy into electrical image ready signal energy for transmission out of the body, said image ready signal adapted to be viewed on an image display, said CMOS image sensor being carried on said elongate member adjacent said optically clear penetrating distal end;

b3) an objective lens carried on said elongate member optically clear penetrating distal end on an optical axis and focusing an image corresponding to an endoscope field of view at an image plane intersecting said optical axis, said CMOS image sensor pixels being disposed in said image plane and on said optical axis;

c) said elongate member being slidably carried in said portal sleeve; and d) said elongate penetrating member having an electrical contact on its proximal end in sliding engagement with another electrical contact for transmitting said image signal from the CMOS sensor to the image display.

7. The penetrating endoscope of claim 6, further including a light source carried by said elongate member and illuminating the endoscope field of view.

8. The penetrating endoscope of claim 6, further including at least one fixed focus objective lens element having a depth of field with a selected minimum in-focus distance for an in-focus image at the image plane.

9. The penetrating endoscope of claim 8, further including a color mosaic optical filter disposed between said CMOS image sensor and said objective lens, said color mosaic optical filter being disposed on said optical axis.

10. A penetrating endoscope for viewing while penetrating anatomical tissue, organs or other objects in the body, comprising:
   a) a portal sleeve housing having an exterior wall enclosing an interior volume;
   b) a handle carried on said portal sleeve housing; said handle adapted to be grasped and manipulated by hand;
   c) an elongate hollow portal sleeve having a longitudinal axis, a proximal end carried by said portal sleeve housing, a distal end for being disposed in the body and an open lumen extending from said proximal end through said distal end, said elongate hollow portal sleeve being adapted to be inserted into the body;
   d) a penetrating member having an axially elongate body terminated proximally and carried by a penetrating member housing, and terminated distally in an optically clear penetrating tip, said elongate body extending through at least a portion of said hollow portal sleeve;
   e) a substantially planar first complementary metal oxide semiconductor (CMOS) image sensor including a plurality of pixels and a pixel signal processing circuit generating an image ready signal, converting image light energy into electrical image ready signal energy, for transmission out of the body, said image ready signal adapted to be viewed on an image display, said CMOS image sensor being carried on said elongate body adjacent said optically clear penetrating distal tip;
   f) an objective lens carried on said penetrating member elongate body distal end on an optical axis and focusing an image corresponding to an endoscope field of view at an image plane intersecting said optical axis, said CMOS image sensor pixels being disposed in said image plane and on said optical axis; and
   g) said portal sleeve comprising a second CMOS image sensor.

11. The penetrating endoscope of claim 10, further including a color mosaic optical filter disposed between said endoscope CMOS image sensor and said objective lens, said color mosaic optical filter being disposed on said optical axis.

12. The penetrating endoscope of claim 10, further including at least one fixed focus objective lens element having a depth of field with a selected minimum in-focus distance for an in-focus image at the image plane.

13. A penetrating endoscope for providing visualization while penetrating organ or tissue structures or foreign objects in the body, comprising:
   an elongate member having a longitudinal axis, a proximal end for being disposed externally and a sharp, optically clear distal end for being disposed in the body, said elongate member being adapted to be inserted through a portal in the body;
   a substantially planar complementary metal oxide semiconductor (CMOS) image sensor including a plurality of pixels and a pixel signal processing circuit generating a color image ready signal, converting image light energy into electrical color image ready signal energy, for transmission out of the body, said color image ready signal adapted to be viewed on a color image display;
   said CMOS image sensor being carried on said elongate member adjacent said elongate member optically clear distal end;
   an objective lens carried on said elongate member distal end on an optical axis and focusing an image corresponding to an endoscope filed of view at an image plane intersecting said optical axis, said CMOS image sensor being mounted with said CMOS image sensor pixels disposed substantially in said image plane and on said optical axis;
   a color mosaic optical filter disposed between said CMOS image sensor and said objective lens, said color mosaic filter being disposed on said optical axis; and
   said elongate member having an electrical contact on its proximal end in sliding engagement with another electrical contact for transmitting said image signal from the CMOS sensor to the image display.

14. The penetrating endoscope of claim 13, further including a source of illumination carried by said penetrating endoscope elongate member and illuminating the endoscope field of view.

15. The penetrating endoscope of claim 13, further including at least one fixed focus objective lens element having a depth of field with a selected minimum in-focus distance for an in-focus image at the image plane.

16. The endoscope of claim 15, further comprising a penetrating tip having a selected length from said image plane to said distal, sharp tip substantially equal to or greater than said minimum in-focus distance, wherein said tip is in focus, as visualized with said image sensor.

17. A penetrating endoscope for viewing anatomical tissue, organs or other objects, in the body comprising:
   a) a portal sleeve housing having an exterior wall enclosing an interior volume;
   b) an elongate hollow portal sleeve having a longitudinal axis, a proximal end carried by said sleeve housing externally, a distal end for being disposed in the body and open lumen extending from said proximal end through said distal end, said elongate hollow portal sleeve being adapted to be inserted into the body;
   c) an endoscope comprising
      c1) an elongate penetrating member having a longitudinal axis, a proximal end and an optically clear penetrating distal end, said elongate member extending through at least a portion of said hollow portal sleeve lumen;
      c2) a substantially planar first complementary metal oxide semiconductor (CMOS) image sensor including a plurality of pixels and a pixel signal processing circuit generating an image ready signal, converting image light energy into electrical image ready signal energy, for transmission out of the body, said image ready signal adapted to be viewed on an image display, said CMOS image sensor being carried on said elongate penetrating member adjacent said optically clear distal end;
      c3) an objective lens carried on said elongate penetrating member distal end on an optical axis and focusing an image corresponding to an endoscope field of view at an image plane intersecting said optical axis, said CMOS image sensor pixels being disposed in said image plane and on said optical axis;
   d) an image display carried on said portal sleeve housing, said image display receiving and displaying said image ready signal generated by said endoscope pixel signal processing circuit; and
   e) said portal sleeve comprising a second CMOS image sensor.

18. The penetrating endoscope of claim 17, further including a repositionable mount affixed to said portal sleeve housing and carrying said image display.

19. The penetrating endoscope of claim 17, wherein said image display is a Liquid Crystal Display (LCD).

20. The penetrating endoscope of claim 17, wherein said image display is a plasma display.

21. The penetrating endoscope of claim 17, wherein said image display is a color, solid state, CMOS display.

22. The penetrating endoscope of claim 21, further including a color mosaic optical filter disposed between said endoscope CMOS image sensor and said objective lens, said color mosaic optical filter being disposed on said optical axis.

23. The penetrating endoscope of claim 17, further including at least one fixed focus objective lens element having a depth of field with a selected minimum in-focus distance for an in-focus image at the image plane.

24. A penetrating endoscope for viewing anatomical issue, organs or other objects in the body comprising:
   a) a portal sleeve housing having an exterior wall enclosing an interior volume;
   b) an elongate hollow portal sleeve having a longitudinal axis, a proximal end carried by said housing externally, a distal end for being disposed in the body and an open lumen extending from said proximal end through said distal end, said elongate hollow portal sleeve being adapted to be inserted into the body;
   c) an endoscope comprising
      c1) an elongate penetrating member having a longitudinal axis, a proximal end carried by a penetrating member hosing and an optically clear penetrating distal end, said elongate member extending through at least a portion of said hollow portal sleeve lumen;
      c2) a substantially planar first complementary metal oxide semiconductor (CMOS) image sensor including a plurality of pixels and a pixel signal processing circuit generating an image ready signal, converting image light energy into electrical image ready signal energy, for transmission out of the body, said image ready signal adapted to be viewed on an image display, said CMOS image sensor being carried on said elongate member adjacent said optically clear distal end;
      c3) an objective lens carried on said elongate penetrating member distal end on an optical axis and focusing an image corresponding to an endoscope field of view at an image plane intersecting said optical axis, said CMOS image sensor pixels being disposed in said image plane and on said optical axis;
   d) an image display carried on said penetrating member housing, said image display receiving and displaying said image ready signal generated by said endoscope pixel processing circuit; and
   e) said portal sleeve comprising a second CMOS image sensor.

25. The penetrating endoscope of claim 24, further including a repositionable mount affixed to said penetrating member housing and carrying said image display.

26. The penetrating endoscope of claim 24, wherein said image display is a Liquid Crystal Display (LCD).

27. The penetrating endoscope of claim 24, wherein said image display is a plasma display.

28. The penetrating endoscope of claim 24, wherein said image display is a color, solid state, CMOS display.

29. The penetrating endoscope of claim 28, further including a color mosaic optical filter disposed between said endoscope CMOS image sensor and said objective lens, said color mosaic optical filter being disposed on said optical axis.

30. The penetrating endoscope of claim 24, further including at least one fixed focus objective lens element having a depth of field with a selected minimum in-focus distance for an in-focus image at the image plane.

31. The penetrating endoscope for viewing anatomical tissue, organs or other objects in the body, comprising:
   a) a portal sleeve housing having an exterior wall enclosing an exterior volume;
   b) an elongate tubular portal sleeve having side wall a longitudinal axis, a proximal end carried by said housing externally, a portal sleeve distal end for being disposed in the body and an open lumen extending from said portal sleeve proximal end through said portal sleeve distal end, said elongate hollow portal sleeve being adapted to be inserted into the body;
   c) an endoscope comprising
      c1) a substantially planar complementary metal oxide semiconductor (CMOS) image sensor including a plurality of pixels and a pixel signal processing circuit generating an image ready signal, converting image light energy into electrical image ready signal energy, for transmission out of the body, said image ready signal adapted to be viewed on an image display; said CMOS image sensor being carried on said elongate tubular portal sleeve side wall, adjacent said portal sleeve distal end;
      c2) an objective lens carried on said elongate tubular portal sleeve side wall adjacent said portal sleeve distal end on an optical axis and focusing an image corresponding to an endoscope field of view at an image plane intersecting said optical axis, said CMOS image sensor pixels being disposed in said image plane and on said optical axis;
   d) an image display carried on said portal sleeve housing, said image display receiving and displaying said image ready signal generated by said endoscope pixel signal processing circuit; and
   e) said portal sleeve having an electrical contact on its proximal end in sliding engagement with another electrical contact for transmitting said image signal from the CMOS sensor to the image display.

32. The penetrating endoscope of claim 31, further including a repositionable mount carrying said image display.

33. The penetrating endoscope of claim 31, wherein said image display is a Liquid Crystal Display (LCD).

34. The penetrating endoscope of claim 31, wherein said image display is a plasma display.

35. The penetrating endoscope of claim 31, wherein said image display is a solid state, CMOS color display.

36. The penetrating endoscope of claim 35, further including a color mosaic optical filter disposed between said endoscope CMOS image sensor and said objective lens, said color mosaic optical filter being disposed on said optical axis.

37. The penetrating endoscope of claim 31, further including at least one fixed focus objective lens element having a depth of field with a selected minimum in-focus distance for an in-focus image at the image plane.

38. An endoscope for providing visualization of organ or tissue structures or foreign objects in the body, comprising:
   an elongated member having a longitudinal axis, a proximal end for being disposed externally and a distal end for being disposed in the body, said elongate member being adapted to be inserted through a portal into the body;
   a substantially planar complementary metal oxide semiconductor (CMOS) image sensor including a plurality of pixels and a pixel signal processing circuit generating a color image ready signal, converting image light energy into electrical color image ready signal energy, for transmission out of the body said color image ready signal adapted to be viewed on a color image display, said CMOS image sensor being carried on said elongate member adjacent said elongate member distal end;

an objective lens carried on said elongate member distal end on an optical axis and focusing an image corresponding to an endoscope field of view at an image plane intersecting said optical axis, said CMOS image sensor being mounted with said CMOS image sensor pixels disposed substantially in said image plane and on said optical axis; and said elongate member having an electrical contact on its proximal end in sliding engagement with another electrical contact for transmitting said image signal from the CMOS sensor to the image display.

39. The endoscope of claim 38, further including a source of illumination carried by said endoscope elongate member and illuminating the endoscope field of view.

40. The endoscope of claim 38, further comprising:
at least one fixed focus objective lens element having a depth of field with a selected minimum in-focus distance for an in-focus image at the image plane; and
a cutting end effector having a selected length substantially equal to or greater than said minimum in-focus distance.

41. The endoscope of claim 40, further including a color mosaic optical filter disposed between said CMOS image sensor and said objective lens, said color mosaic optical filter being disposed on said optical axis.

42. The endoscope of claim 38, further including at least one fixed focus objective lens element having a depth of field with a selected minimum in-focus distance for an in-focus image at the image plane.

43. The endoscope of claim 42, further comprising a surgical instrument and effectors having a selected length substantially equal to or greater than said minimum in-focus distance.

44. The endoscope of claim 42, further including a color mosaic optical filter disposed between said CMOS image sensor and said objective lens, said color mosaic optical filter being disposed on said optical axis.

45. A surgical endoscope instrument for viewing anatomical tissue or organ structures or other objects in the body, comprising:
a) an elongate hollow barrel having a longitudinal axis, a proximal end for being disposed externally and a distal end for being disposed in the body and an open lumen extending from said proximal end through said distal end, said elongate hollow barrel being adapted to be inserted through a portal into the body;
b) an endoscope comprising
b1) an elongate member having a longitudinal axis, a proximal end and a distal end, said elongate member extending through at least a portion of said hollow barrel lumen;
b2) a substantially planar complementary metal oxide semiconductor (CMOS) image sensor including a plurality of pixels and a pixel signal processing circuit generating an image ready signal, converting image light energy into electrical image ready signal energy, for transmission out of the body, said image ready signal adapted to be viewed on an image display; said CMOS image sensor being carried on said elongate member adjacent said distal end;
b3) an objective lens carried on said elongate member distal end on an optical axis and focusing an image corresponding to an endoscope field of view at an image plane intersecting said optical axis, said CMOS image sensor pixels being disposed in said image plane and on said optical axis; and
c) said elongate member being slidably carried in said barrel and having an electrical contact on its proximal end in sliding engagement with another electrical contact for transmitting said image signal from the CMOS sensor to the image display.

46. The instrument of claim 45, further comprising a cutter carried on said barrel distal end.

47. The instrument of claim 46, further including at least one fixed focus objective lens element having a depth of field with a selected minimum in-focus distance for an in-focus image at the image plane;
said cutter having a selected length equal to or greater than said minimum in-focus distance.

48. The instrument of claim 45, further including a light source carried by said elongate member and illuminating the endoscope field of view.

49. The instrument of claim 45, further including at least one fixed focus objective lens element having a depth of field with a selected minimum in-focus distance for an in-focus image at the image plane.

50. The endoscope of claim 49, further including a color mosaic optical filter disposed between said CMOS image sensor and said objective lens, said color mosaic optical filter being disposed on said optical axis.

51. The instrument of claim 49, further comprising a surgical instrument end effector carried by said elongate hollow barrel, said end effector having a selected length being substantially equal to or greater than said endoscope minimum in-focus distance.

52. A surgical endoscopic instrument for viewing and manipulating anatomical tissue or other objects in the body, comprising:
a) an elongate member having a longitudinal axis, a proximal end for being disposed externally and a distal end for being disposed in the body, said elongate member adapted to be inserted through a portal into the body and having an end effector of a selected length carried on said elongate member distal end;
b) a substantially planar complementary metal oxide semiconductor (CMOS) image sensor including a plurality of pixels and a pixel signal processing circuit generating an image ready signal, converting image light energy into electrical image ready signal energy, for transmission out of the body, said image ready signal adapted to be viewed on an image display, said CMOS image sensor being carried on said elongate member adjacent said distal end;
c) an objective lens carried on said elongate member distal end on an optical axis and focusing an image corresponding to an endoscope field of view at an image plane intersecting said optical axis, said CMOS image sensor pixels being disposed in said image plane and on said optical axis;
d) a light source carried by said elongate member and illuminating the endoscope field of view; and
e) said elongate member having an electrical contact on its proximal end in sliding engagement with another electrical contact for transmitting said image signal from the CMOS sensor to the image display.

53. The endoscope of claim 52, further including a color mosaic optical filter disposed between said CMOS image sensor and said objective lens, said color mosaic optical filter being disposed on said optical axis.

54. The instrument of claim 52, further including at least one fixed focus objective lens element having a depth of field with a selected minimum in-focus distance for an in-focus image at the image plane, said minimum in-focus distance being less than or substantially equal to said end effector selected length.

55. The instrument of claim 54, wherein said end effector is a cutting instrument for excising, incising or dissecting anatomical tissue or other objects, in the body, comprising first and second opposable cutting jaws hingedly mounted on said elongate member distal end; said jaws having said selected end effector length.

56. The instrument of claim 54, wherein said end effector is a forceps instrument for viewing and manipulating anatomical tissue or other objects, in the body, comprising first and second opposable forceps jaws hingedly mounted on said elongate member distal end; said jaws having said selected end effector length.

57. The instrument of claim 56, further including a housing carrying said elongate member proximal end, said housing carrying at least one handle, at least one of said jaws being responsive to handle.

58. An endoscopic forceps instrument for viewing and manipulating anatomical tissue, organs or other objects in the body, comprising:
   a) a housing having an exterior wall enclosing an interior volume;
   b) at least one articulable handle carried on said housing; said handle adapted to be grasped and manipulated by hand;
   c) an elongate hollow barrel having a longitudinal axis, a proximal end for being carried by said housing externally, a distal end for being disposed in the body and an open lumen extending from said proximal end through a portal into the body;
   d) first and second opposable forceps jaws hingedly mounted on said elongate hollow barrel distal end; at least one of said forceps jaws being responsive to said handle, said jaws having a selected length;
   e) an endoscope comprising
      e1) an elongate member having a longitudinal axis, a proximal end and a distal end, said elongate member extending through at least apportion of said hollow barrel lumen;
      e2) a substantially planar first complementary metal oxide semiconductor (CMOS) image sensor including plurality of pixels and a pixel signal processing circuit generating an image ready signal, converting image light energy into electrical image ready signal energy, for transmission out of the body, said image ready signal adapted to be viewed on an image display, said CMOS image sensor being carried on said elongate member adjacent said distal end;
      e3) an objective lens carried on said elongate member distal end on an optical axis and focusing an image corresponding to an endoscope field of view at an image plane intersecting said optical axis, said CMOS image sensor pixels being disposed in said image plane and on said optical axis;
   f) said elongate member being slidably and rotatably carried in said barrel; and
   g) said housing comprising a second CMOS image sensor.

59. The endoscopic forceps instrument of claim 58, wherein said first and second opposable jaws are cutting jaws.

60. The endoscopic forceps instrument of claim 58, further including a color mosaic optical filter disposed between said endoscope CMOS image sensor and said objective lens, said color mosaic filter being disposed on said optical axis.

61. The instrument of claim 58, further including at least one fixed focus objective lens element having a depth of field with a selected minimum in-focus distance for an in-focus image at the image plane, said minimum in-focus distance being less than or substantially equal to said forceps jaw selected length.

62. An endoscope for providing visualization of organ or tissue structures or foreign objects in the body, comprising:
   an elongate member having a longitudinal axis, a proximal end for being disposed externally and a distal end for being disposed in the body, said elongate member being adapted to be inserted through a portal into the body;
   a substantially planar complementary metal oxide semiconductor (CMOS) image sensor including a plurality of pixels and a pixel signal processing circuit generating a color image ready signal, converting image light energy into electrical color image ready signal energy, for transmission out of body, said color image ready signal adapted to be viewed on a color image display, said CMOS image sensor being carried on said elongate member adjacent said elongate member distal end;
   an objective lens carried on said elongate member distal end on an optical axis and focusing an image corresponding to an endoscope field of view at an image plan intersecting said optical axis, said CMOS image sensor being mounted with said CMOS image sensor pixels disposed substantially in said image plane and on said optical axis;
   a color mosaic optical filter disposed between said CMOS image sensor and said objective lends, said color mosaic optical filter being disposed on said optical axis; and
   said elongate member having an electrical contact on its proximal end in sliding engagement with another electrical contact for transmitting said image signal from the CMOS sensor to the image display.

63. The endoscope of claim 62, further including a source of illumination carried by said endoscope elongate member and illuminating the endoscope field of view.

64. The endoscope of claim 62, further including at least one fixed focus objective lens element having a depth of field with a selected minimum in-focus distance for an in-focus image at the image plane.

65. The endoscope of claim 64, further comprising a surgical instrument end effector having a selected length substantially equal to or greater than said minimum in-focus distance.

66. The endoscope of claim 65, wherein said end effector comprises first and second forceps jaws; said forceps jaws having a length substantially equal to or greater than said minimum in-focus distance.

67. An endoscopic instrument for viewing anatomical tissue, organs or other objects in the body, comprising:
   a) a housing having an exterior wall enclosing an interior volume;
   b) an elongate hollow barrel having a longitudinal axis, a proximal end carried by said housing externally, a distal end for being disposed in the body and an open lumen extending from said proximal end through said distal end, said elongate hollow barrel being adapted to be inserted through a portal into the body;

c) an endoscope comprising
  c1) an elongate member having a longitudinal axis, a proximal end and a distal end, said elongate member extending through at least a portion of said hollow barrel lumen;
  c2) a substantially planar first complementary metal oxide semiconductor (CMOS) image sensor including a plurality of pixels and a pixel signal processing circuit generating an image ready signal, converting image light energy into electrical image ready signal energy, for transmission out of the body, said image ready signal adapted to be viewed on an image display, said CMOS image sensor being carried on said elongate member adjacent said distal end;
  c3) an objective lends carried on said elongate member distal end on an optical axis and focusing an image corresponding to an endoscope field of view at an image plane intersecting said optical axis, said CMOS image sensor pixels being disposed in said image plane and on said optical axis; and
d) an image display carried on said housing, said image display receiving and displaying said image ready signal generated by said endoscope pixel signal processing circuit, and said housing comprising a second CMOS image sensor.

68. The endoscopic instrument of claim 67, further including a repositionable mount carrying said image display.

69. An endoscopic instrument for viewing anatomical tissue, organs or other objects in the body, comprising:
a) a housing having an exterior wall enclosing an interior volume;
b) an elongate hollow barrel having a longitudinal axis, a proximal end carried by said housing externally, a distal end for being disposed in the body and an open lumen extending from said proximal end through said distal end, said elongate hollow barrel being adapted to be inserted through a portal into the body;
c) an endoscope comprising
  c1) an elongate member having a longitudinal axis, a proximal end and a distal end, said elongate member extending through at least a portion of said hollow barrel lumen;
  c2) a substantially planar complementary metal oxide semiconductor (CMOS) image sensor including a plurality of pixels and a pixel signal processing circuit generating an image ready signal, converting image light energy into electrical image ready signal energy, for transmission out of the body, said image ready signal adapted to be viewed on an image display, said CMOS image sensor being carried on said elongate member adjacent said distal end;
  c3) an objective lens carried on said elongate member distal end on an optical axis and focusing an image corresponding to an endoscope field of view at an image plane intersecting said optical axis, said CMOS image sensor pixels being disposed in said image plane and on said optical axis;
d) an image display carried on said housing, said image display receiving and displaying said image ready signal generated by said endoscope pixel signal processing circuit; and
e) a repositionable mount carrying said image display, wherein said repositionable mount comprises a flexible stalk supporting an image display.

70. The endoscopic instrument of claim 68, further including an electrical connector release-ably connecting said image display with said endoscopic pixel signal processing circuit.

71. The endoscopic instrument of claim 67, wherein said image display is a Liquid Crystal Display (LCD).

72. The endoscopic instrument of claim 67, wherein said image display is a plasma display.

73. The endoscopic instrument of claim 67, wherein said image display is a color display.

74. The endoscopic instrument of claim 67, further including a color mosaic optical filter disposed between said endoscope CMOS image sensor and said objective lens, said color mosaic optical filter being disposed on said optical axis.

75. The instrument of claim 67, further comprising a surgical instrument end effector carried by said elongate hollow barrel, said end effector having a selected length.

76. The instrument of claim 75, further including at least one fixed focus objective lens element having a depth of field with a selected minimum in-focus distance for an in-focus image at the image plane, said minimum in-focus distance being less than or substantially equal to said end effector selected length.

77. An endoscopic instrument for viewing anatomical tissue, organs or other objects in the body, comprising:
a) a housing having an exterior wall enclosing an interior volume;
b) an elongate member having a longitudinal axis, a proximal end carried by said housing externally, a distal end for being disposed in the body and an open lumen extending from said proximal end through said distal end, an elongate hollow barrel being adapted to be inserted through a portal into the body;
c) an endoscope comprising
  c1) a substantially planar first complementary metal oxide semiconductor (CMOS) image sensor including a plurality of pixels and a pixel signal processing circuit generating an image ready signal, converting image light energy into electrical image ready signal energy, for transmission out of the body, said image ready signal adapted to be viewed on an image display, said CMOS image sensor being carried on said elongate member adjacent said distal end;
  c2) an objective lens carried on said elongate member distal end on an optical axis and focusing an image corresponding to an endoscope field of view at an image plane intersecting said optical axis, said CMOS image sensor pixels being disposed in said image plane and on said optical axis;
d) an image display carried on said housing, said image display receiving and displaying said image ready signal generated by said endoscope pixel signal processing circuit; and
e) said housing comprising a second CMOS image sensor.

78. The endoscopic instrument of claim 77, further including a repositionable mount carrying said image display.

79. The endoscopic instrument for viewing anatomical tissue, organs or other objects in the body, comprising:
a) a housing having an exterior wall enclosing an interior volume;
b) an elongate member having a longitudinal axis, a proximal end carried by said housing externally, a distal end for being disposed in the body and an open lumen extending from said proximal end through said distal end, an [said] elongate hollow barrel being adapted to be inserted through a portal into the body;

c) an endoscope comprising
  c1) a substantially planar complementary metal oxide semiconductor (CMOS) image sensor including a plurality of pixels and a pixel signal processing circuit generating an image ready signal, converting image light energy into electrical image ready signal energy, for transmission out of the body, said image ready signal adapted to be viewed on an image display, said CMOS image sensor being carried on said elongate member adjacent said distal end;
  c2) an objective lens carried on said elongate member distal end on an optical axis and focusing an image corresponding to an endoscope field of view at an image plane intersecting said optical axis, said CMOS image sensor pixels being disposed in said image plane and on said optical axis; and
d) an image display carried on said housing, said image display receiving and displaying said image ready signal generated by said endoscope pixel signal processing circuit, wherein said repositionable mount comprises a flexible stalk supporting an image display.

80. The endoscopic instrument of claim 77, further including an electrical connector release-ably connecting said image display with said endoscope pixel signal processing circuit.

81. The endoscopic instrument of claim 77, wherein said image display is a Liquid Crystal Display (LCD).

82. The endoscopic instrument of claim 77, wherein said image display is a plasma display.

83. The endoscopic instrument of claim 77, wherein said image display is a color display.

84. The endoscopic instrument of claim 77, further including a color mosaic optical filter disposed between said endoscope CMOS image sensor and said objective lens, said color mosaic optical filter being disposed on said optical axis.

85. The instrument of claim 77, further comprising a surgical instrument end effector carried by said elongate hollow barrel, said end effector having a selected length.

86. The instrument of claim 85, further including at least one fixed focus objective lens element having a depth of field with a selected minimum in-focus distance for an in-focus image at the image plane, said minimum in-focus distance being less than or substantially equal to said end effector selected length.

87. An endoscopic instrument for viewing of anatomical tissue, organs or other objects in the body, comprising:

a) a housing having an exterior wall enclosing an interior volume;
b) an elongate hollow barrel having a longitudinal axis, a proximal end carried by said housing externally, a distal end for being disposed in the body and an open lumen extending from said proximal end through said distal end, and a cutting end effector having a selected length; said elongate hollow barrel being adapted to be inserted through a portal into the body;
c) an endoscope comprising
  c1) an elongate member having a longitudinal axis, a proximal end and a distal end, aid elongate member extending through at least a portion of said hollow barrel lumen;
  c2) a substantially planar complementary metal oxide semiconductor (CMOS) image sensor including a plurality of pixels and a pixel signal processing circuit generating an image signal, converting image light energy into electrical image ready signal energy, for transmission out of the body, said image ready signal adapted to be viewed on an image display, said CMOS image sensor being carried on said elongate member adjacent said distal end;
  c3) an objecting lens carried on said elongate member distal end on an optical axis and focusing an image corresponding to an endoscope field of view at an image plane intersecting said optical axis, said CMOS image sensor pixels being disposed in said image plane and on said optical axis;
d) an image display carried on said housing, said image display receiving and displaying said image ready signal generated by said endoscope pixel signal processing circuit; and
e) said elongate member having an electrical contact on its proximal end in sliding engagement with another electrical contact for transmitting said image signal from the CMOS sensor to the image display.

88. The instrument of claim 87, further including at least one fixed focus objective lens element having a depth of field with a selected minimum in-focus distance for an in-focus image at the image plane, said minimum in-focus distance being less than or substantially equal to said cutting end effector selected length.

* * * * *